US012478412B2

(12) United States Patent
Cromer et al.

(10) Patent No.: US 12,478,412 B2
(45) Date of Patent: Nov. 25, 2025

(54) REDUCER LOCKING MECHANISMS AND METHODS OF USE

(71) Applicant: MEDOS INTERNATIONAL SARL, Le Locle (CH)

(72) Inventors: Christopher M. Cromer, Boston, MA (US); Richard Fournier, New Bedford, MA (US); Eric Biester, Barrington, RI (US)

(73) Assignee: Medos International Sàrl, Le Locle (CH)

( * ) Notice: Subject to any disclaimer, the term of this patent is extended or adjusted under 35 U.S.C. 154(b) by 462 days.

(21) Appl. No.: 17/989,797

(22) Filed: Nov. 18, 2022

(65) Prior Publication Data

US 2023/0157736 A1 May 25, 2023

Related U.S. Application Data

(60) Provisional application No. 63/406,137, filed on Sep. 13, 2022, provisional application No. 63/281,506, filed on Nov. 19, 2021.

(51) Int. Cl.

| | |
|---|---|
| ***A61B 17/70*** | (2006.01) |
| ***A61B 17/128*** | (2006.01) |
| *A61B 17/00* | (2006.01) |

(52) U.S. Cl.

CPC ...... *A61B 17/7086* (2013.01); *A61B 17/1285* (2013.01); *A61B 2017/00407* (2013.01)

(58) Field of Classification Search

None

See application file for complete search history.

(56) References Cited

U.S. PATENT DOCUMENTS 410,780 A 9/1889 Cahn
1,470,313 A 10/1923 Woolen
(Continued)

FOREIGN PATENT DOCUMENTS

CN 102488548 B 9/2013
DE 4238339 C2 10/1994
(Continued)

OTHER PUBLICATIONS

International Search Report and Written Opinion for Application No. PCT/EP2021/081168, mailed May 12, 2022 (11 pages).
(Continued)

*Primary Examiner* — Jan Christopher L Merene
(74) *Attorney, Agent, or Firm* — Barnes & Thornburg LLP

(57) ABSTRACT

Disclosed are reducer instrument locking mechanisms. They can be located near a center pivot joint of the reducer, thereby eliminating a ratchet at the reducer proximal end. The locking mechanisms can include a pawl or latch that travels with one handle from an open position to a closed position. The pawl can fall into a groove formed in an opposing handle such that handles of the reducer can be locked relative to one another, at least with regard to movement of the handles away from one another. When falling into the groove, the pawl can create an auditory and/or tactile indication that a sufficient amount of rod reduction has been achieved to allow for set screw insertion. After set screw insertion, the reducer locking mechanisms can be released to clear it of the groove and allow the reducer to return to its open position.

18 Claims, 25 Drawing Sheets

(56) References Cited

U.S. PATENT DOCUMENTS

| | | | |
|---|---|---|---|
| 1,628,144 | A | 5/1927 | Herrmann |
| 1,709,766 | A | 4/1929 | Bolton |
| 1,889,330 | A | 11/1932 | Humes et al. |
| 1,925,385 | A | 9/1933 | Humes et al. |
| 2,113,246 | A | 4/1938 | Wappler |
| 2,248,054 | A | 7/1941 | Becker |
| 2,248,057 | A | 7/1941 | Bond |
| 2,291,413 | A | 7/1942 | Siebrandt |
| 2,370,407 | A | 2/1945 | Mccartney |
| 2,800,820 | A | 7/1957 | Retterath |
| 3,960,147 | A | 6/1976 | Murray |
| 4,237,875 | A | 12/1980 | Termanini |
| 4,271,836 | A | 6/1981 | Bacal et al. |
| 4,411,259 | A | 10/1983 | Drummond |
| 4,445,513 | A | 5/1984 | Ulrich et al. |
| 4,655,223 | A | 4/1987 | Kim |
| 4,809,695 | A | 3/1989 | Gwathmey et al. |
| 4,896,661 | A | 1/1990 | Bogert et al. |
| 5,014,407 | A | 5/1991 | Boughten et al. |
| 5,020,519 | A | 6/1991 | Hayes et al. |
| D343,000 | S | 1/1994 | Olson |
| D346,217 | S | 4/1994 | Sparker et al. |
| 5,306,248 | A | 4/1994 | Barrington |
| 5,364,397 | A | 11/1994 | Hayes et al. |
| 5,391,170 | A | 2/1995 | McGuire et al. |
| 5,429,641 | A | 7/1995 | Gotfried |
| 5,431,658 | A | 7/1995 | Moskovich |
| 5,484,440 | A | 1/1996 | Allard |
| 5,545,165 | A | 8/1996 | Biedermann et al. |
| 5,551,320 | A | 9/1996 | Horobec et al. |
| 5,616,143 | A | 4/1997 | Schlapfer et al. |
| 5,649,931 | A | 7/1997 | Bryant et al. |
| 5,672,175 | A | 9/1997 | Martin |
| 5,683,399 | A | 11/1997 | Jones |
| 5,697,933 | A | 12/1997 | Gundlapalli et al. |
| 5,707,371 | A | 1/1998 | Metz-Stavenhagen |
| D390,954 | S | 2/1998 | Kumar et al. |
| 5,720,751 | A | 2/1998 | Jackson |
| 5,725,532 | A | 3/1998 | Shoemaker |
| 5,746,757 | A | 5/1998 | McGuire |
| 5,782,831 | A | 7/1998 | Sherman et al. |
| 5,810,878 | A | 9/1998 | Burel et al. |
| 5,910,141 | A | 6/1999 | Morrison et al. |
| 5,941,885 | A | 8/1999 | Jackson |
| 5,951,564 | A | 9/1999 | Schroder et al. |
| 5,951,579 | A | 9/1999 | Dykes |
| 6,010,509 | A | 1/2000 | Delgado et al. |
| 6,036,692 | A | 3/2000 | Burel et al. |
| 6,099,528 | A | 8/2000 | Saurat |
| 6,123,707 | A | 9/2000 | Wagner |
| 6,139,549 | A | 10/2000 | Keller |
| 6,183,472 | B1 | 2/2001 | Lutz |
| 6,210,330 | B1 | 4/2001 | Tepper |
| 6,251,112 | B1 | 6/2001 | Jackson |
| 6,258,090 | B1 | 7/2001 | Jackson |
| 6,371,973 | B1 | 4/2002 | Tepper |
| 6,413,258 | B1 | 7/2002 | Bernhardt, Jr. |
| 6,440,133 | B1 | 8/2002 | Beale et al. |
| 6,440,142 | B1 | 8/2002 | Ralph et al. |
| 6,440,144 | B1 | 8/2002 | Bacher |
| 6,511,484 | B2 | 1/2003 | Torode et al. |
| 6,530,929 | B1 | 3/2003 | Justis et al. |
| 6,554,832 | B2 | 4/2003 | Shluzas |
| 6,589,249 | B2 | 7/2003 | Sater et al. |
| 6,648,888 | B1 | 11/2003 | Shluzas |
| 6,660,006 | B2 | 12/2003 | Markworth et al. |
| 6,676,661 | B1 | 1/2004 | Martin Benlloch et al. |
| 6,726,692 | B2 | 4/2004 | Bette |
| 6,743,231 | B1 | 6/2004 | Gray et al. |
| 6,746,449 | B2 | 6/2004 | Jones et al. |
| 6,752,832 | B2 | 6/2004 | Neumann |
| 6,755,829 | B1 | 6/2004 | Bono et al. |
| 6,790,208 | B2 | 9/2004 | Oribe et al. |
| 6,790,209 | B2 | 9/2004 | Beale et al. |
| 6,827,722 | B1 | 12/2004 | Schoenefeld |
| 7,081,117 | B2 | 7/2006 | Bono et al. |
| 7,083,621 | B2 | 8/2006 | Shaollan et al. |
| 7,090,677 | B2 | 8/2006 | Fallin et al. |
| 7,156,849 | B2 | 1/2007 | Dunbar et al. |
| 7,179,254 | B2 | 2/2007 | Pendekanti et al. |
| 7,179,261 | B2 | 2/2007 | Sicvol et al. |
| 7,189,234 | B2 | 3/2007 | Zucherman et al. |
| 7,278,995 | B2 | 10/2007 | Nichols et al. |
| 7,320,689 | B2 | 1/2008 | Keller |
| 7,371,239 | B2 | 5/2008 | Dec et al. |
| 7,462,182 | B2 | 12/2008 | Lim |
| 7,481,813 | B1 | 1/2009 | Purcell |
| 7,485,120 | B2 | 2/2009 | Ray |
| 7,491,207 | B2 | 2/2009 | Keyer et al. |
| 7,527,638 | B2 | 5/2009 | Anderson et al. |
| 7,572,281 | B2 | 8/2009 | Runco et al. |
| 7,621,918 | B2 | 11/2009 | Jackson |
| 7,651,502 | B2 | 1/2010 | Jackson |
| 7,666,188 | B2 | 2/2010 | Anderson et al. |
| 7,708,763 | B2 | 5/2010 | Selover et al. |
| 7,776,040 | B2 | 8/2010 | Markworth et al. |
| 7,806,912 | B2 | 10/2010 | Lawton et al. |
| 7,824,411 | B2 | 11/2010 | Varieur et al. |
| 7,824,413 | B2 | 11/2010 | Varieur et al. |
| 7,842,044 | B2 | 11/2010 | Runco et al. |
| 7,867,237 | B2 | 1/2011 | Stad et al. |
| 7,887,539 | B2 | 2/2011 | Dunbar, Jr. et al. |
| 7,887,541 | B2 | 2/2011 | Runco et al. |
| 7,901,434 | B2 | 3/2011 | Drewry et al. |
| 7,922,724 | B2 | 4/2011 | Lim |
| 7,931,677 | B2 | 4/2011 | Abdelgany |
| 7,988,698 | B2 | 8/2011 | Rosenberg et al. |
| 8,109,974 | B2 | 2/2012 | Boomer et al. |
| 8,172,847 | B2 | 5/2012 | Dziedzic et al. |
| 8,192,438 | B2 | 6/2012 | Garamszegi |
| 8,216,241 | B2 | 7/2012 | Runco et al. |
| 8,235,997 | B2 | 8/2012 | Hoffman et al. |
| 8,246,657 | B1 | 8/2012 | Samuel |
| 8,298,269 | B2 | 10/2012 | Null et al. |
| 8,303,595 | B2 | 11/2012 | Jones |
| 8,308,774 | B2 | 11/2012 | Hoffman et al. |
| 8,317,837 | B2 | 11/2012 | Rezach et al. |
| 8,337,527 | B2 | 12/2012 | Hawkins et al. |
| 8,343,165 | B2 | 1/2013 | Berrevoets |
| 8,377,104 | B2 | 2/2013 | Jones et al. |
| 8,394,109 | B2 | 3/2013 | Hutton et al. |
| 8,430,916 | B1 | 4/2013 | Winslow et al. |
| 8,439,922 | B1 | 5/2013 | Arnold et al. |
| 8,460,308 | B2 | 6/2013 | Marino et al. |
| 8,540,718 | B2 | 9/2013 | Dauster et al. |
| 8,556,904 | B2 | 10/2013 | Rezach et al. |
| 8,603,145 | B2 | 12/2013 | Forton et al. |
| 8,617,165 | B2 | 12/2013 | Harper |
| 8,636,742 | B2 | 1/2014 | Runco et al. |
| 8,636,776 | B2 | 1/2014 | Rosenberg et al. |
| 8,647,347 | B2 | 2/2014 | Runco et al. |
| 8,657,857 | B2 | 2/2014 | Dall et al. |
| 8,685,029 | B2 | 4/2014 | Dziedzic et al. |
| 8,715,323 | B2 | 5/2014 | Ballard et al. |
| 8,728,124 | B2 | 5/2014 | Miller |
| 8,747,409 | B2 | 6/2014 | Ichelmann et al. |
| 8,764,756 | B2 | 7/2014 | Jones |
| 8,790,348 | B2 | 7/2014 | Stad et al. |
| 8,795,283 | B2 | 8/2014 | Petit |
| 8,828,056 | B2 | 9/2014 | Buss et al. |
| 8,845,640 | B2 | 9/2014 | McLean et al. |
| 8,845,649 | B2 | 9/2014 | Jackson |
| 8,870,881 | B2 | 10/2014 | Rezach et al. |
| 8,876,869 | B1 | 11/2014 | Schafer et al. |
| 8,900,240 | B2 | 12/2014 | White et al. |
| 8,906,062 | B2 | 12/2014 | Nichols et al. |
| 8,932,296 | B2 | 1/2015 | Neary et al. |
| 8,951,289 | B2 | 2/2015 | Matityahu |
| 8,956,362 | B2 | 2/2015 | Landry et al. |
| 8,979,848 | B2 | 3/2015 | Butters et al. |
| 8,986,349 | B1 | 3/2015 | German et al. |
| 9,044,272 | B2 | 6/2015 | Shaffrey et al. |
| 9,044,274 | B2 | 6/2015 | Gunn et al. |
| 9,078,705 | B2 | 7/2015 | Matthis et al. |

(56) References Cited

U.S. PATENT DOCUMENTS

| | | | |
|---|---|---|---|
| 9,078,709 | B2 | 7/2015 | McBride |
| 9,084,634 | B1 | 7/2015 | Lab et al. |
| 9,119,674 | B2 | 9/2015 | Matthis et al. |
| 9,125,694 | B2 | 9/2015 | Butler et al. |
| 9,149,307 | B2 | 10/2015 | Sandstrom et al. |
| 9,155,567 | B2 | 10/2015 | Auerbach et al. |
| 9,186,188 | B2 | 11/2015 | Gleason et al. |
| 9,204,901 | B2 | 12/2015 | Black et al. |
| 9,204,909 | B2 | 12/2015 | Rezach et al. |
| 9,220,543 | B2 | 12/2015 | Walker et al. |
| 9,247,969 | B2 | 2/2016 | Nunley et al. |
| 9,254,150 | B2 | 2/2016 | Biedermann et al. |
| 9,265,533 | B2 | 2/2016 | Nelson et al. |
| 9,265,538 | B2 | 2/2016 | Stad et al. |
| 9,271,768 | B2 | 3/2016 | Artaki et al. |
| 9,283,002 | B2 | 3/2016 | Larroque-Lahitette et al. |
| 9,308,030 | B2 | 4/2016 | Manninen |
| 9,451,994 | B1 | 9/2016 | Whipple et al. |
| 9,486,256 | B1 | 11/2016 | Lish et al. |
| 9,492,205 | B2 | 11/2016 | Alsup et al. |
| 9,498,261 | B2 | 11/2016 | McClintock |
| 9,795,417 | B2 | 10/2017 | Beger et al. |
| 10,039,578 | B2 | 8/2018 | Anderson et al. |
| 10,238,432 | B2 | 3/2019 | Carruth et al. |
| 10,299,839 | B2 | 5/2019 | Sicvol et al. |
| 10,398,476 | B2 | 9/2019 | Lee et al. |
| D914,210 | S | 3/2021 | Koros |
| 10,966,762 | B2 | 4/2021 | Lee et al. |
| 11,291,481 | B2 | 4/2022 | Schmura et al. |
| 11,291,482 | B2 | 4/2022 | Schmura et al. |
| D1,004,774 | S | 11/2023 | Schmura et al. |
| 11,832,855 | B2 | 12/2023 | Lee et al. |
| 2001/0029376 | A1 | 10/2001 | Sater et al. |
| 2002/0072752 | A1 | 6/2002 | Zucherman et al. |
| 2002/0095153 | A1 | 7/2002 | Jones et al. |
| 2003/0009168 | A1 | 1/2003 | Beale et al. |
| 2003/0028195 | A1 | 2/2003 | Bette |
| 2003/0083747 | A1 | 5/2003 | Winterbottom et al. |
| 2003/0125750 | A1 | 7/2003 | Zwirnmann et al. |
| 2003/0149438 | A1 | 8/2003 | Nichols et al. |
| 2003/0171756 | A1 | 9/2003 | Fallin et al. |
| 2003/0191370 | A1 | 10/2003 | Phillips |
| 2003/0199872 | A1 | 10/2003 | Markworth et al. |
| 2003/0208203 | A1 | 11/2003 | Lim et al. |
| 2003/0225408 | A1 | 12/2003 | Nichols et al. |
| 2004/0049191 | A1 | 3/2004 | Markworth et al. |
| 2004/0147936 | A1 | 7/2004 | Rosenberg et al. |
| 2004/0147937 | A1 | 7/2004 | Dunbar, Jr. et al. |
| 2004/0172057 | A1 | 9/2004 | Guillebon et al. |
| 2004/0176779 | A1 | 9/2004 | Casutt et al. |
| 2004/0220567 | A1 | 11/2004 | Elsermann et al. |
| 2004/0254576 | A1 | 12/2004 | Dunbar, Jr. et al. |
| 2004/0267275 | A1 | 12/2004 | Coumoyer et al. |
| 2005/0015094 | A1 | 1/2005 | Keller |
| 2005/0015095 | A1 | 1/2005 | Keller |
| 2005/0033299 | A1 | 2/2005 | Shluzas |
| 2005/0051648 | A1 | 3/2005 | Mercier |
| 2005/0055031 | A1 | 3/2005 | Lim |
| 2005/0059969 | A1 | 3/2005 | McKinley |
| 2005/0079909 | A1 | 4/2005 | Singhaseni |
| 2005/0090824 | A1 | 4/2005 | Shluzas et al. |
| 2005/0131408 | A1 | 6/2005 | Sicvol et al. |
| 2005/0131420 | A1 | 6/2005 | Techiera et al. |
| 2005/0131421 | A1 | 6/2005 | Anderson et al. |
| 2005/0131422 | A1 | 6/2005 | Anderson et al. |
| 2005/0143749 | A1 | 6/2005 | Zalenski et al. |
| 2005/0149036 | A1 | 7/2005 | Varieur et al. |
| 2005/0149048 | A1 | 7/2005 | LePort et al. |
| 2005/0149053 | A1 | 7/2005 | Varieur et al. |
| 2005/0192570 | A1 | 9/2005 | Jackson |
| 2005/0192579 | A1 | 9/2005 | Jackson |
| 2005/0228392 | A1 | 10/2005 | Keyer et al. |
| 2005/0261702 | A1 | 11/2005 | Oribe et al. |
| 2006/0009775 | A1 | 1/2006 | Dec et al. |
| 2006/0025768 | A1 | 2/2006 | Iott et al. |
| 2006/0036254 | A1 | 2/2006 | Lim |
| 2006/0036260 | A1 | 2/2006 | Runco et al. |
| 2006/0069391 | A1 | 3/2006 | Jackson |
| 2006/0074418 | A1 | 4/2006 | Jackson |
| 2006/0079892 | A1 | 4/2006 | Roychowdhury et al. |
| 2006/0079909 | A1 | 4/2006 | Runco et al. |
| 2006/0089651 | A1 | 4/2006 | Trudeau et al. |
| 2006/0095035 | A1 | 5/2006 | Jones et al. |
| 2006/0111712 | A1 | 5/2006 | Jackson |
| 2006/0111713 | A1 | 5/2006 | Jackson |
| 2006/0111730 | A1 | 5/2006 | Hay |
| 2006/0166534 | A1 | 7/2006 | Brumfield et al. |
| 2006/0166535 | A1 | 7/2006 | Brumfield et al. |
| 2006/0229611 | A1 | 10/2006 | Avery et al. |
| 2006/0233597 | A1 | 10/2006 | Ensign et al. |
| 2006/0293692 | A1 | 12/2006 | Whipple et al. |
| 2007/0093849 | A1 | 4/2007 | Jones et al. |
| 2007/0100347 | A1 | 5/2007 | Stad et al. |
| 2007/0129731 | A1 | 6/2007 | Sicvol et al. |
| 2007/0161998 | A1 | 7/2007 | Whipple |
| 2007/0167954 | A1 | 7/2007 | Sicvol et al. |
| 2007/0173831 | A1 | 7/2007 | Abdou |
| 2007/0185375 | A1 | 8/2007 | Stad et al. |
| 2007/0213722 | A1 | 9/2007 | Jones et al. |
| 2007/0233097 | A1 | 10/2007 | Anderson et al. |
| 2007/0260261 | A1 | 11/2007 | Runco et al. |
| 2007/0270817 | A1 | 11/2007 | Rezach |
| 2007/0270880 | A1 | 11/2007 | Lindemann et al. |
| 2007/0282337 | A1 | 12/2007 | Garamszegi |
| 2008/0015601 | A1 | 1/2008 | Castro et al. |
| 2008/0058805 | A1 | 3/2008 | Stuart |
| 2008/0077134 | A1 | 3/2008 | Dziedzic et al. |
| 2008/0077135 | A1 | 3/2008 | Stad et al. |
| 2008/0154277 | A1 | 6/2008 | Machalk et al. |
| 2008/0195155 | A1 | 8/2008 | Hoffman et al. |
| 2008/0228233 | A1 | 9/2008 | Hoffman et al. |
| 2008/0243190 | A1 | 10/2008 | Dziedzic et al. |
| 2008/0255574 | A1 | 10/2008 | Dye |
| 2009/0030419 | A1 | 1/2009 | Runco et al. |
| 2009/0030420 | A1 | 1/2009 | Runco et al. |
| 2009/0054902 | A1 | 2/2009 | Mickiewicz et al. |
| 2009/0082811 | A1 | 3/2009 | Stad et al. |
| 2009/0088764 | A1 | 4/2009 | Stad et al. |
| 2009/0105712 | A1 | 4/2009 | Dauster et al. |
| 2009/0138056 | A1 | 5/2009 | Anderson et al. |
| 2009/0143828 | A1 | 6/2009 | Stad et al. |
| 2009/0312804 | A1 | 12/2009 | Gamache et al. |
| 2010/0121385 | A1 | 5/2010 | Blain et al. |
| 2010/0137915 | A1 | 6/2010 | Anderson et al. |
| 2011/0034961 | A1 | 2/2011 | Runco et al. |
| 2011/0034962 | A1 | 2/2011 | Dunbar, Jr. et al. |
| 2011/0093022 | A1 | 4/2011 | Runco et al. |
| 2011/0144695 | A1 | 6/2011 | Rosenberg et al. |
| 2011/0208254 | A1 | 8/2011 | Villa et al. |
| 2012/0029571 | A1 | 2/2012 | Schwab et al. |
| 2012/0053643 | A1 | 3/2012 | Harper |
| 2012/0078308 | A1* | 3/2012 | Dziedzic ............ A61B 17/7086 606/279 |
| 2012/0143265 | A1 | 6/2012 | Biedermann et al. |
| 2012/0179214 | A1 | 7/2012 | Geist et al. |
| 2012/0191144 | A1 | 7/2012 | Peultier et al. |
| 2012/0203291 | A1 | 8/2012 | Boulaine |
| 2012/0253413 | A1 | 10/2012 | Runco et al. |
| 2013/0018419 | A1 | 1/2013 | Rezach et al. |
| 2013/0066385 | A1 | 3/2013 | Benoist |
| 2013/0079826 | A1 | 3/2013 | Simonson |
| 2013/0085534 | A1 | 4/2013 | Hainard et al. |
| 2013/0123854 | A1 | 5/2013 | Kondrashov et al. |
| 2013/0245702 | A1 | 9/2013 | McBride |
| 2013/0261679 | A1* | 10/2013 | McBride .............. A61B 17/708 606/86 A |
| 2014/0012337 | A1 | 1/2014 | Biedermann et al. |
| 2014/0018858 | A1 | 1/2014 | Laeng et al. |
| 2014/0058464 | A1 | 2/2014 | Hutchens |
| 2014/0074106 | A1 | 3/2014 | Shin |
| 2014/0094858 | A1 | 4/2014 | Picetti et al. |
| 2014/0114363 | A1 | 4/2014 | Stevenson et al. |
| 2014/0148865 | A1 | 5/2014 | Hennard et al. |
| 2014/0163625 | A1 | 6/2014 | Meyer et al. |

(56) References Cited

U.S. PATENT DOCUMENTS

| | | | |
|---|---|---|---|
| 2014/0180298 | A1 | 6/2014 | Stevenson et al. |
| 2014/0276896 | A1 | 9/2014 | Harper |
| 2014/0277160 | A1 | 9/2014 | Ziolo |
| 2014/0277170 | A1 | 9/2014 | Barrett et al. |
| 2014/0277206 | A1 | 9/2014 | Reitblat et al. |
| 2014/0296862 | A1 | 10/2014 | Stad et al. |
| 2014/0311264 | A1 | 10/2014 | Black et al. |
| 2014/0316475 | A1 | 10/2014 | Parikh et al. |
| 2015/0057707 | A1 | 2/2015 | Barrus et al. |
| 2015/0066042 | A1 | 3/2015 | Cummins et al. |
| 2015/0100097 | A1 | 4/2015 | Barrus |
| 2015/0100098 | A1 | 4/2015 | Moore |
| 2015/0105832 | A1 | 4/2015 | Gleason et al. |
| 2015/0112397 | A1 | 4/2015 | Petit |
| 2015/0173803 | A1 | 6/2015 | Droulout |
| 2015/0182265 | A1 | 7/2015 | Biedermann et al. |
| 2015/0196328 | A1 | 7/2015 | Hirschl et al. |
| 2015/0201971 | A1 | 7/2015 | Gaines et al. |
| 2015/0257798 | A1 | 9/2015 | Biedermann et al. |
| 2015/0359568 | A1 | 12/2015 | Rezach |
| 2016/0022317 | A1 | 1/2016 | Kraus |
| 2016/0066967 | A1 | 3/2016 | Jackson et al. |
| 2016/0151093 | A1 | 6/2016 | Barry et al. |
| 2016/0242825 | A1 | 8/2016 | Simpson et al. |
| 2017/0265901 | A1 | 9/2017 | Hawkins et al. |
| 2017/0333087 | A1 | 11/2017 | Lee et al. |
| 2017/0333088 | A1 | 11/2017 | Lee et al. |
| 2018/0014858 | A1 | 1/2018 | Biester et al. |
| 2018/0161073 | A1 | 6/2018 | Lee et al. |
| 2018/0185072 | A1 | 7/2018 | Rubin et al. |
| 2018/0228518 | A1 | 8/2018 | Carruth et al. |
| 2018/0280062 | A1 | 10/2018 | Lee et al. |
| 2019/0117280 | A1 | 4/2019 | Avidano et al. |
| 2019/0193541 | A1 | 6/2019 | Takeda |
| 2020/0297395 | A1 | 9/2020 | Schmura et al. |
| 2020/0297396 | A1 | 9/2020 | Schmura et al. |
| 2021/0059725 | A1 | 3/2021 | Avidano et al. |
| 2021/0177469 | A1 | 6/2021 | Lee et al. |
| 2022/0142683 | A1 | 5/2022 | Manson et al. |
| 2024/0065736 | A1 | 2/2024 | Lee et al. |

FOREIGN PATENT DOCUMENTS

| | | | |
|---|---|---|---|
| DE | 29806563 | U1 | 6/1998 |
| EP | 0948939 | B1 | 5/2004 |
| EP | 1648320 | A2 | 4/2006 |
| EP | 1796564 | A1 | 6/2007 |
| EP | 2004079 | B1 | 7/2013 |
| FR | 2677242 | A1 | 12/1992 |
| FR | 2680314 | B1 | 11/1993 |
| FR | 2729291 | B1 | 9/1997 |
| WO | 1996021396 | A1 | 7/1996 |
| WO | 2002080787 | A2 | 10/2002 |
| WO | 2003028566 | A1 | 4/2003 |
| WO | 2005006948 | A2 | 1/2005 |
| WO | 2005058173 | A1 | 6/2005 |
| WO | 2006020443 | A1 | 2/2006 |
| WO | 2010045301 | A1 | 4/2010 |
| WO | 2023089096 | A1 | 5/2023 |

OTHER PUBLICATIONS

International Preliminary Report on Patentability for Application No. PCT/EP2021/081168, mailed May 9, 2023 (8 pages).

U.S. Appl. No. 18/503,455, filed Nov. 7, 2023, Unilateral Implant Holders and Related Methods, Medos International Sarl.

International Search Report and Written Opinion for PCT/US2018/065497, mailed Jul. 8, 2019 (20 pages).

International Search Report and Written Opinion for PCT/EP2022/084215, mailed Mar. 15, 2023 (18 pages).

* cited by examiner

REDUCER LOCKING MECHANISMS AND METHODS OF USE

CROSS-REFERENCE TO RELATED APPLICATIONS

This application claims the benefit of U.S. Provisional Application No. 63/281,506, filed Nov. 19, 2021. This application also claims the benefit of U.S. Provisional Application No. 63/406,137, filed Sep. 13, 2022. The entire contents of each of these applications are hereby incorporated by reference in their entirety.

FIELD

This disclosure relates generally to locking mechanisms for surgical instruments and related methods of use and, more particularly, to locking mechanisms for reducers utilized to approximate two components, e.g., a spinal fixation element and a bone anchor during spine surgery.

BACKGROUND

Fixation systems can be used in orthopedic surgery or neurosurgery to maintain a desired spatial relationship between multiple bones or bone fragments. For example, in spine surgery, a spinal fixation system can be implanted into a patient to align and/or fix a desired orientation of one or more vertebrae. A typical spinal fixation system can include implants, such as bone anchors, disposed in the vertebrae and a spinal fixation element, such as a rod, that is secured to the implants by closure mechanisms, such as set screws. Implanting the fixation system can involve multiple steps, e.g., surgical site preparation, bone anchor implantation, derotation, rod introduction and reduction, set screw insertion, and others.

Rod reduction and set screw management can be a challenging part of posterior spinal fixation procedures and current rod reduction instrumentation has several shortcomings. For example, in some cases handheld reducer instruments can be utilized that employ opposed handles that pivot toward one another to reduce a rod into a receiving portion of a bone anchor or other implant. In order to avoid requiring a user to maintain constant pressure on the opposed handles, such instruments can include a lock to maintain their position. Prior instruments often utilize a lock that includes a large and long ratchet with multiple teeth located at a proximal end of the opposed handles. In such configurations a number of challenges can be present. For example, the long ratchet disposed at a proximal end of the device can be prone to binding due to misalignment between the opposed handles, e.g., due to forces exerted thereon during use. Further, the ratchet can obscure a surgeon or other user's view, as well as interfere with gripping and actuation of the instrument or introduction of other components to the surgical site. Moreover, the multiple ratchet teeth can make it difficult to determine when the rod is sufficiently reduced to allow for insertion of a bone anchor locking mechanism, such as a set screw. This is because the ratchet lock can engage with one or more teeth before the rod is reduced far enough to allow for set screw insertion. Still further, the ratchet lock can be difficult to disengage, as one or more teeth can catch and prevent continued removal as the opposed handles are separated after use. Finally, ratchet locks using a plurality of teeth can be difficult to manufacture, given the often large number of teeth and need for precision machining.

Accordingly, there is a need for improved locking mechanisms for use with reducers that address challenges with work flow, usability, and manufacturing of said devices.

SUMMARY

Disclosed herein are locking mechanisms and related methods of use for reducer instruments, e.g., handheld acute reducers and others. The locking mechanisms disclosed herein can be located adjacent to a center pivot joint of the reducer, thereby eliminating the use of a large, long ratchet at the proximal end of the instrument near where a surgeon or other user typically grasps the instrument. The locking mechanisms disclosed herein can include a pawl or latch that travels with one instrument handle during actuation from an initial, open position to a closed position. The pawl can fall into a groove formed in an opposing handle such that handles of the reducer can be locked in place relative to one another, at least with regard to movement of the handles away from one another. When falling into the groove, the pawl can create an auditory and/or tactile indication that a sufficient amount of rod reduction has been achieved to allow for set screw or other closure mechanism insertion. After set screw insertion or other locking of the implant is performed, the reducer locking mechanisms disclosed herein can be released by pressing a button coupled to the pawl to clear it of the groove and allow the reducer to return to its initial, open position.

In one aspect, a surgical instrument includes a first handle having a proximal grip portion and a distal housing with a lumen extending therethrough. The instrument further includes opposed arms extending distally from the housing that are configured to interface with an implant. The instrument also includes a reducer sleeve disposed around the opposed arms and configured to translate relative thereto, as well as a second handle having a proximal grip portion. The second handle can be pivotably coupled to the housing and the reducer sleeve such that moving the second handle toward the first handle causes distal translation of the reducer sleeve relative to the opposed arms. The instrument further includes a pawl pivotably coupled to the second handle distal to the grip portion. The pawl can be configured to ride over a portion of the housing that includes a groove as the second handle is moved toward the first handle. Further, the pawl can be configured to seat in the groove and maintain a relative position of the first and second handles when the second handle is moved sufficiently toward the first handle.

Any of a variety of alternative or additional features can be included and are considered within the scope of the present disclosure. For example, in some embodiments, the instrument can further include a button extending from the pawl and configured to move the pawl clear of the groove when depressed.

In certain embodiments, the instrument can further include a spring urging a distal portion of the pawl into the portion of the housing that includes the groove.

In some embodiments, the opposed arms can define a tapering slot therebetween having a first distance between the opposed arms at a distal portion of the slot that is greater than a second distance between the opposed arms at a proximal portion of the slot.

In certain embodiments, a distal end of at least one of the opposed arms can include a protrusion configured to extend into a recess of the implant.

In some embodiments, distal translation of the reducer sleeve relative to the opposed arms can move the opposed arms toward one another.

In certain embodiments, the instrument can further include one or more links pivotably coupled to the second handle and the reducer sleeve.

In some embodiments, the instrument can further include a biasing element urging the first and second handle away from one another.

In certain embodiments, the housing can include at least one protrusion formed thereon that abuts against the second handle at a fully open or a fully closed position of the first and second handles relative to one another. In some embodiments, the at least one protrusion can include a first protrusion that abuts against the second handle at a fully closed position of the first and second handles, and the first protrusion can be separated from the second handle when the pawl is seated in the groove and maintaining a relative position of the first and second handles.

In some embodiments, each opposed arm can include a movable portion configured to deflect radially inward relative to the arm. Further, in certain embodiments the reducer sleeve can include a feature formed on an inner surface thereof that is configured to contact the movable portion of each opposed arm. In some embodiments, each movable portion can include an inwardly-extending projection.

In another aspect, a surgical method includes positioning opposed arms of a reducer instrument around a portion of an implant, and moving first and second handles of the reducer instrument toward one another until a pawl coupled to the second handle seats within a groove formed in a housing of the first handle to maintain a relative position of the first and second handles. Further, moving the first and second handles of the reducer instrument toward one another can cause a reducer sleeve disposed around the opposed arms to translate distally relative thereto. Still further, distal translation of the reducer sleeve can cause the opposed arms of the reducer instrument to move toward one another and couple with the implant, and also cause a spinal fixation element to translate distally into a receiving portion of the implant.

As with the instruments described above, the methods disclosed herein can include any of a variety of additional or alternative steps that are considered within the scope of the present disclosure. For example, in some embodiments, moving the first and second handles of the reducer instrument toward one another can include overcoming a biasing force urging the handles away from one another.

In some embodiments, the method can further include locking the spinal fixation element relative to the implant while the reducer instrument maintains a position of the spinal fixation element relative to the implant. In certain embodiments, locking the spinal fixation element relative to the implant can include inserting a set screw through a bore formed in the reducer instrument and coupling the set screw with the implant. In some embodiments, the method can further include reducing the spinal fixation element distally into the receiving portion of the implant using the set screw such that compressive forces between the reducer sleeve and spinal fixation element are reduced. In certain embodiments, the method can further include moving the first and second handles of the reducer instrument toward one another beyond a position at which the pawl seats within the groove of the housing until one of the first and second handles contacts a stop formed on the other handle. In some embodiments, the method can further include depressing a button to move the pawl clear of the groove and allow movement of the first and second handles away from one another. In certain embodiments, the method can further include moving the first and second handles of the reducer instrument away from one another to proximally translate the reducer sleeve relative to the opposed arms and allow the opposed arms to move away from one another and release from the implant. Further, in some embodiments the method can further include repeating the method across a plurality of implants disposed along a patient's spine.

In another aspect, a surgical method includes positioning an instrument in an unlocked configuration, where the instrument includes an implant engagement member, a reduction member having a channel therein for receiving the implant engagement member therethrough, a handle assembly being coupled to the reduction member and receiving the implant engagement member through a bore thereof, and a lock having a pawl disposed outside of a groove formed in the handle assembly. Further, the handle assembly can include a pair of handles pivotably coupled to one another. The method can further include positioning an implant between opposed arms of the implant engagement member, and moving the pair of handles toward one another to position the instrument in a locked configuration. Moreover, moving the pair of handles toward one another distally can advance the reduction member relative to the implant engagement member to reduce a spinal fixation element into a receiving portion of the implant and can move the pawl into the groove of the handle assembly.

As with the instruments and methods described above, any of a variety of additional or alternative steps are considered within the scope of the present disclosure. For example, in some embodiments, moving the pair of handles toward one another can include overcoming a biasing force on the pair of handles and causing a linkage disposed between the pair of handles and the reduction member to advance the reduction member distally.

In certain embodiments, the method can further include actuating a button coupled to the pawl to disengage the pawl from the groove and allow return of the device from the locked configuration to the unlocked configuration.

In some embodiments, the method can further include delivering a set screw to the implant through the bore of the handle assembly.

In certain embodiments, distally advancing the reduction member relative to the implant engagement member can deflect movable portions of each of the opposed arms of the implant engagement member radially inward such that the movable portions extend into a recess formed in the implant.

In another aspect, a surgical method includes positioning opposed arms of a reducer instrument around a portion of an implant, and moving first and second handles of the reducer instrument toward one another until a pawl coupled to the second handle seats within a groove formed in a housing of the first handle to maintain a relative position of the first and second handles. Further, moving the first and second handles of the reducer instrument toward one another can cause a reducer sleeve disposed around the opposed arms to translate distally relative thereto. Moreover, distal translation of the reducer sleeve can cause movable portions of the opposed arms of the reducer instrument to move toward one another and couple with the implant, and also cause a spinal fixation element to translate distally into a receiving portion of the implant.

Any of the features or variations described herein can be applied to any particular aspect or embodiment of the present disclosure in a number of different combinations.

The absence of explicit recitation of any particular combination is due solely to avoiding unnecessary length or repetition.

BRIEF DESCRIPTION OF THE DRAWINGS

The aspects and embodiments of the present disclosure can be more fully understood from the following detailed description taken in conjunction with the accompanying drawings, in which.

DETAILED DESCRIPTION

Disclosed herein are locking mechanisms and related methods of use for reducer instruments, e.g., handheld acute reducers and others. The locking mechanisms disclosed herein can be located adjacent to a center pivot joint of the reducer, thereby eliminating the use of a large, long ratchet at the proximal end of the instrument near where a surgeon or other user typically grasps the instrument. The locking mechanisms disclosed herein can include a pawl or latch that travels with one instrument handle during actuation from an initial, open position to a closed position. The pawl can fall into a groove formed in an opposing handle such that handles of the reducer can be locked in place relative to one another, at least with regard to movement of the handles away from one another. When falling into the groove, the pawl can create an auditory and/or tactile indication that a sufficient amount of rod reduction has been achieved to allow for set screw or other closure mechanism insertion. After set screw insertion or other locking of the implant is performed, the reducer locking mechanisms disclosed herein can be released by pressing a button coupled to the pawl to clear it of the groove and allow the reducer to return to its initial, open position.

Certain example embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure. Additionally, to the extent that linear, circular, or other dimensions are used in the description of the disclosed devices and methods, such dimensions are not intended to limit the types of shapes that can be used in conjunction with such devices and methods. Equivalents to such dimensions can be determined for different geometric shapes, etc. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

Figure 1A:
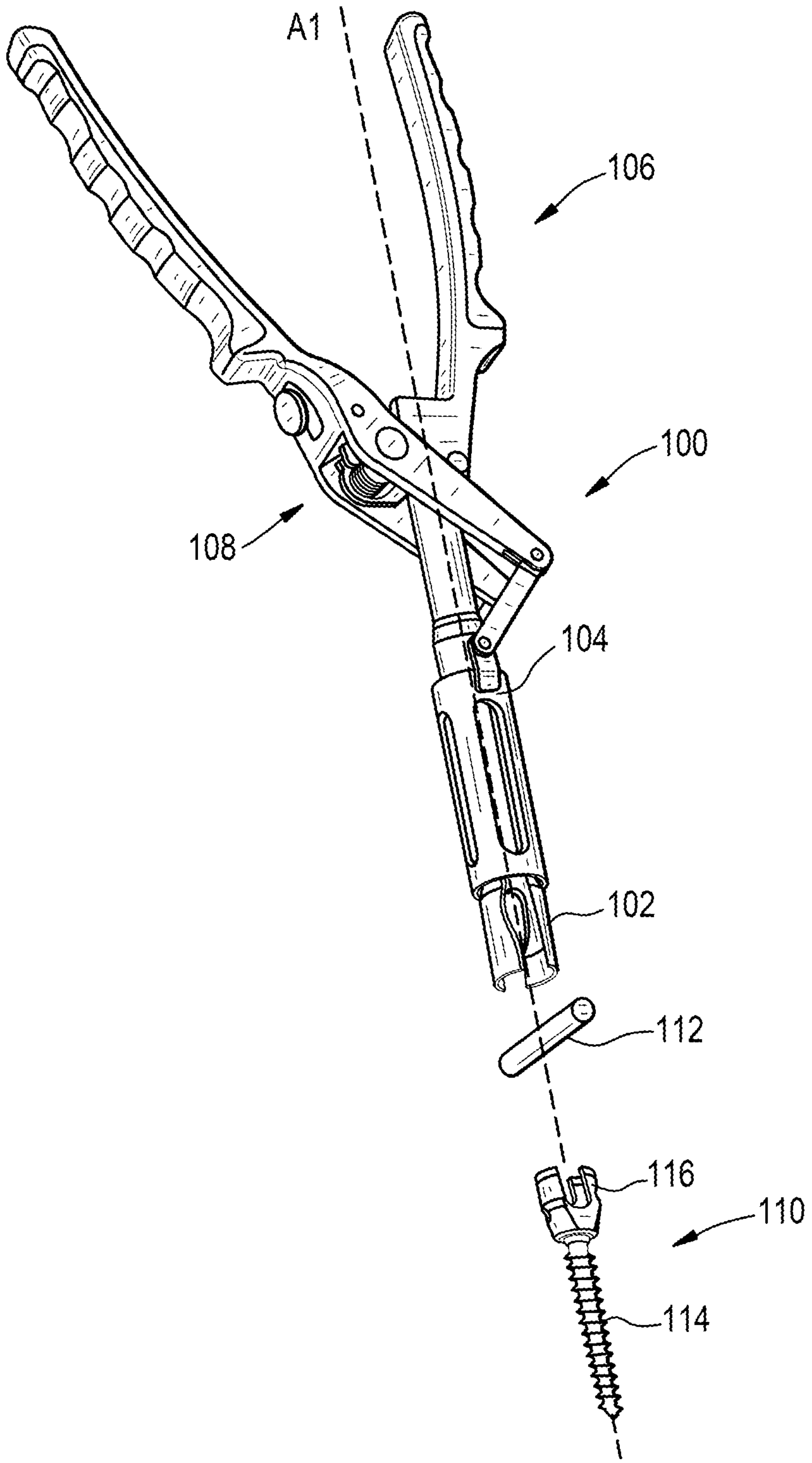
FIG. 1A is a perspective view of one embodiment of a reducer instrument according to the present disclosure.
Figure 1B:
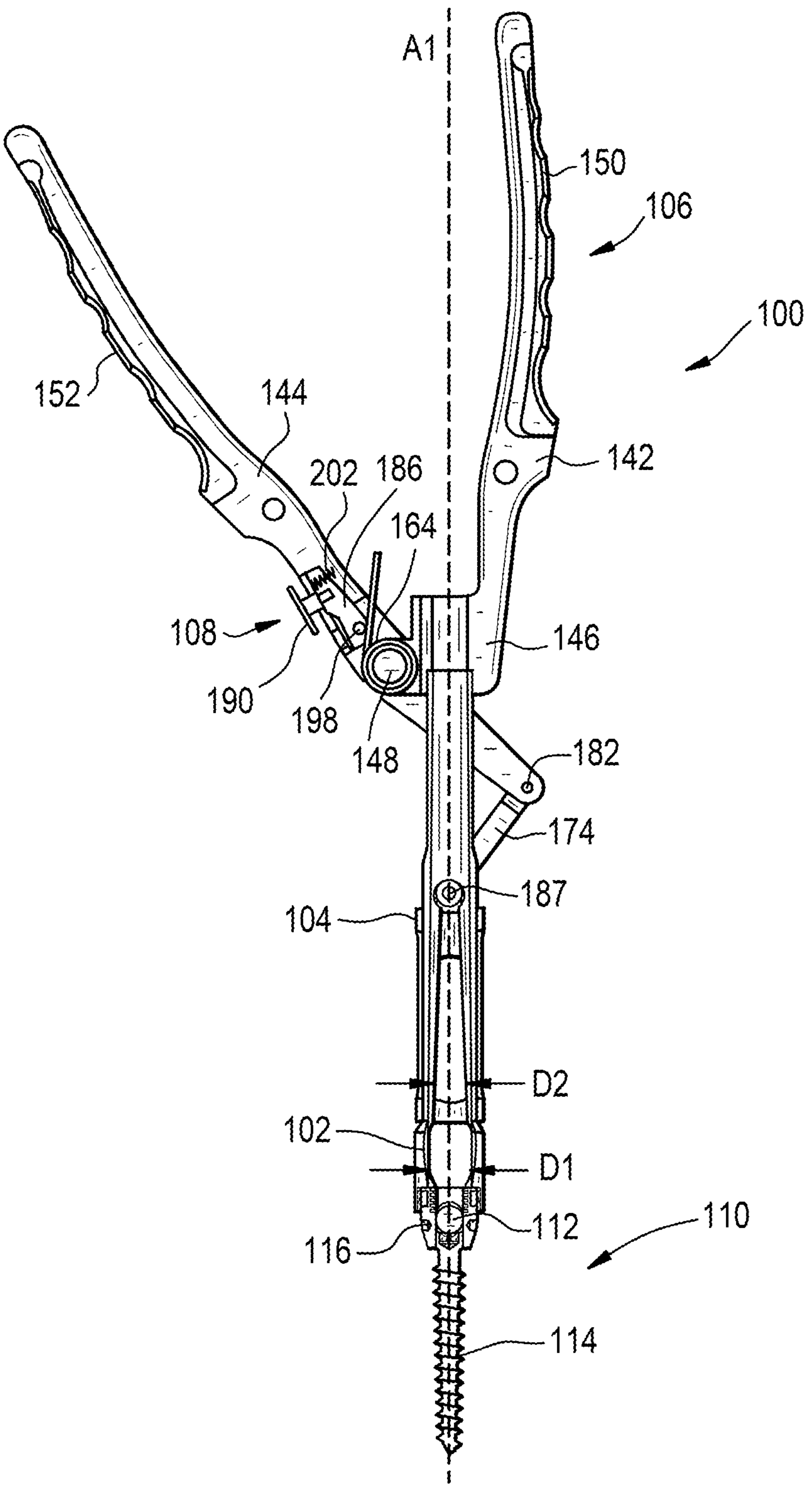
FIG. 1B is longitudinal cross-sectional view of the reducer instrument of FIG. 1A.
Figure 1C:
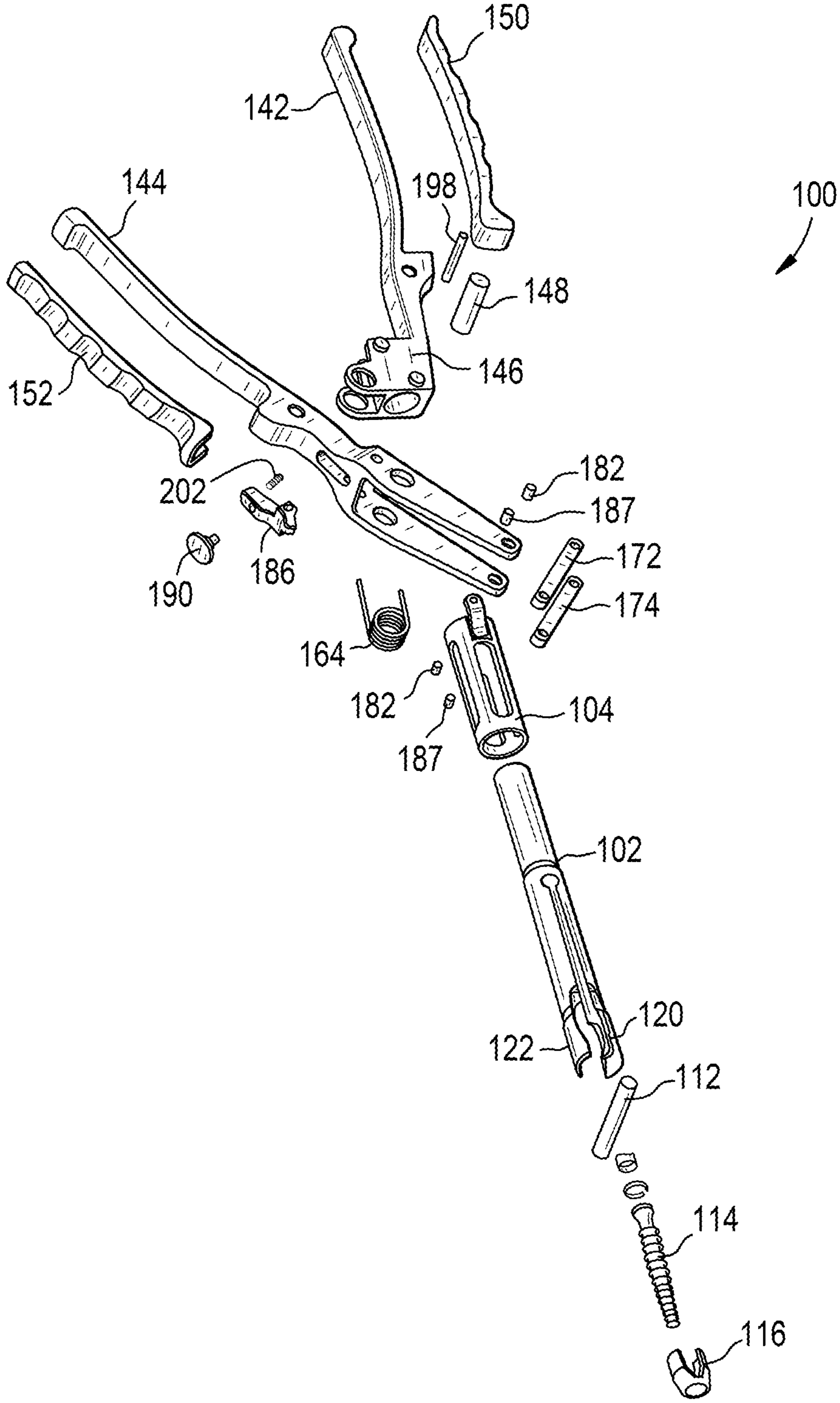
FIG. 1C is an exploded view of the reducer instrument of FIG. 1A.

FIGS. 1A-1C illustrate perspective, longitudinal cross-sectional, and exploded views, respectively, of one embodiment of a reducer instrument 100. The instrument 100 can include an implant engagement member 102, a reduction member 104, a handle assembly 106, and a locking mechanism 108. The implant engagement member 102 can be used to couple and/or otherwise engage an implant, such as a bone anchor 110, that is configured to receive a spinal fixation element, such as a spinal rod 112. The reduction member 104 can be movably coupled to the implant engagement member 102 to reduce the spinal rod 112 into the bone anchor 110 engaged by the implant engagement member 102. The handle assembly 106 can move the reduction member 104 relative to the implant engagement member 102, with the locking mechanism 108 locking the device 100 in place once the rod 112 is sufficiently reduced to allow for the insertion of a closure mechanism, such as a set screw, to lock the position of the rod relative to the bone anchor. The instrument 100 can include bores formed therein to allow insertion of additional instruments, e.g., a set screw inserter, therethrough to deliver and install a closure mechanism.

While various implants and spinal fixation elements can be used, FIGS. 1A-1C illustrate an example embodiment of a bone anchor 110 that can be used with the rod reduction devices disclosed herein. As shown, the bone anchor 110 includes a threaded shank 114 and a rod-receiving head 116. The threaded shank 114 can be configured to be threaded into bone and the rod-receiving head 116 can be configured to receive a spinal fixation element, such as the spinal rod 112. In the illustrated embodiment, the rod-receiving head 116 includes opposed arms that define a u-shaped receiving portion for seating the spinal rod 112. The rod-receiving head 116 can also include mating features formed thereon to facilitate mating with the implant engagement member 102. While various mating features can be used, in one embodiment the rod-receiving head 116 can include one or more recesses (e.g., blind bores, through-bores, grooves, notches, thread forms, etc.) formed in a proximal portion thereof for receiving one or more projections (e.g., pins, nubs, broken or continuous ridges, hooks, thread forms, etc.) formed on the implant engagement member 102, as discussed in more detail below. In certain embodiments, any of a variety of complementary features can be utilized in any configuration (e.g., protrusions or other male features formed on the bone anchor with complementary recesses or female features formed on the instrument, etc.). Other implants can also be used, including, for example, hooks, plates, staples, etc.

Figure 2:
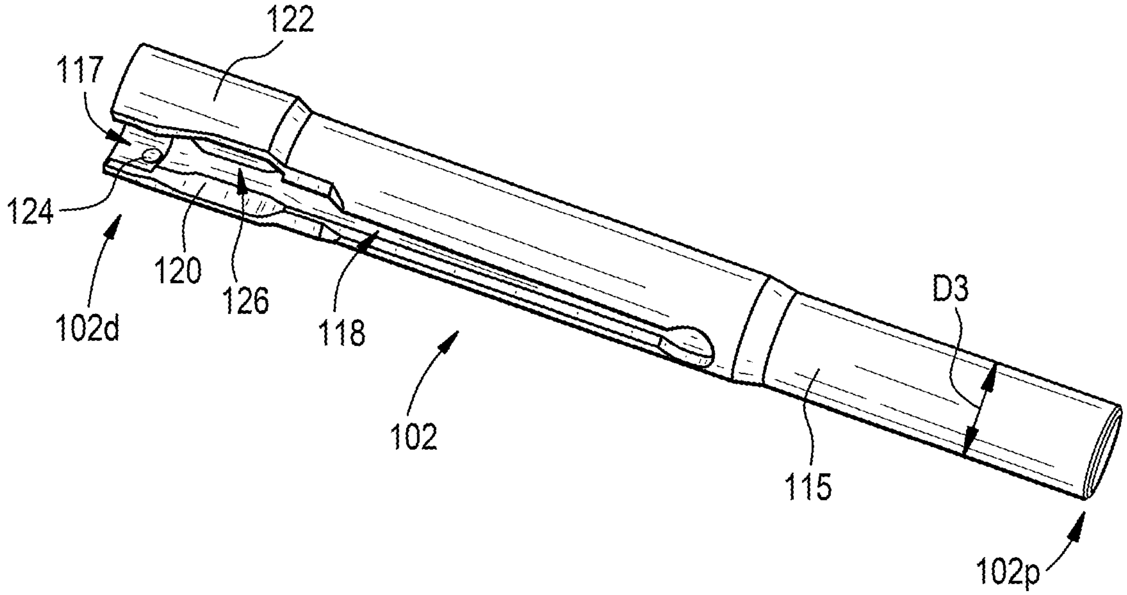
FIG. 2 is a perspective view of an implant engagement member of the reducer instrument of FIG. 1A.

The implant engagement member 102 can be configured to engage at least a portion of the bone anchor 110. For example, as shown in FIG. 2, the implant engagement member 102 can include a proximal portion having an elongate substantially cylindrical portion 115 defining a lumen 117. The lumen 117 extending through the implant engagement member 102 can have any number of openings and its cross-section does not need to form a complete or continuous closed structure, such as an uninterrupted circle, at any point along the length of the implant engagement member 102. For example, as shown, the implant engagement member 102 can include one or more cutouts or slots 118 that extend proximally from the distal end 102*d*. The rod slot 118 can form a pair of opposed arms 120, 122 at the distal end of the implant engagement member 102 that can be configured to engage and couple with the bone anchor 110. The opposed arms 120, 122 can extend generally parallel to one another or can be obliquely angled to one another. As shown in FIG. 1B, the opposed arms in the illustrated embodiment diverge from one another to create an outer circumference that increases in a proximal-to-distal direction along a longitudinal axis A1 of the instrument. This configuration can result in a tapering slot 118 and the arms having a first distance D1 therebetween at a distal portion of the slot that is greater than a second distance D2 between the opposed arms at a proximal portion of the slot. Further, the arms 120, 122 can be configured to move relative to one another, e.g., elastically deform toward or away from one another in response to forces imparted by a reducer sleeve translating along a length of the implant engagement member 102, as described in more detail below. For example, the opposed arms 120, 122 can be configured to flex, e.g., in a radial direction, between a first, relaxed position that facilitates advancement of the arms 120, 122 longitudinally over the rod-receiving head 116, and a second, compressed position wherein the arms 120, 122 are moved toward one another to a position in which the arms 120, 122 provide a radially compressive force onto the rod-receiving head 116, thereby coupling the bone anchor 110 to the instrument 100. In some embodiments, the arms can be configured such that they clear a bone anchor receiving head 116 when in the first, relaxed configuration such that the instrument can be distally advanced over a proximal portion of the receiver head without needing to impart large axial forces to deflect the arms over the head, as is required with many prior devices.

The opposed arms 120, 122 can also include various features to facilitate mating to the bone anchor 110. For example, one or more of the opposed arms 120, 122 can include at least one mating element 124 disposed on an inner surface thereof. By way of a non-limiting example, the mating element can be in the form of at least one projection that is configured to extend into at least one recess formed in the rod-receiving head 116, as noted above. The size, shape, and number of mating elements 124 formed on each arm 120, 122 can vary depending on the configuration of the bone anchor 110 and the type of connection desired. In other embodiments, rather than having opposed arms 120, 122, the implant engagement member 102 can include any number of arms, or can have other configurations for engaging the bone anchor 110.

Figure 4A:
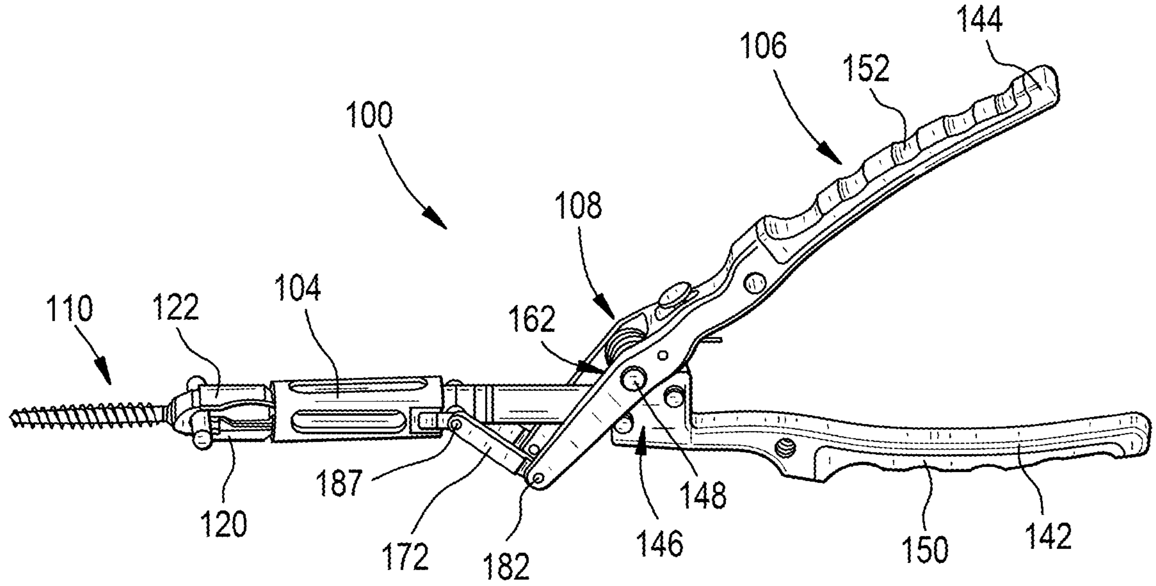
FIG. 4A is a side perspective view of the instrument of FIG. 1A in an initial, open position or unlocked configuration.
Figure 4B:
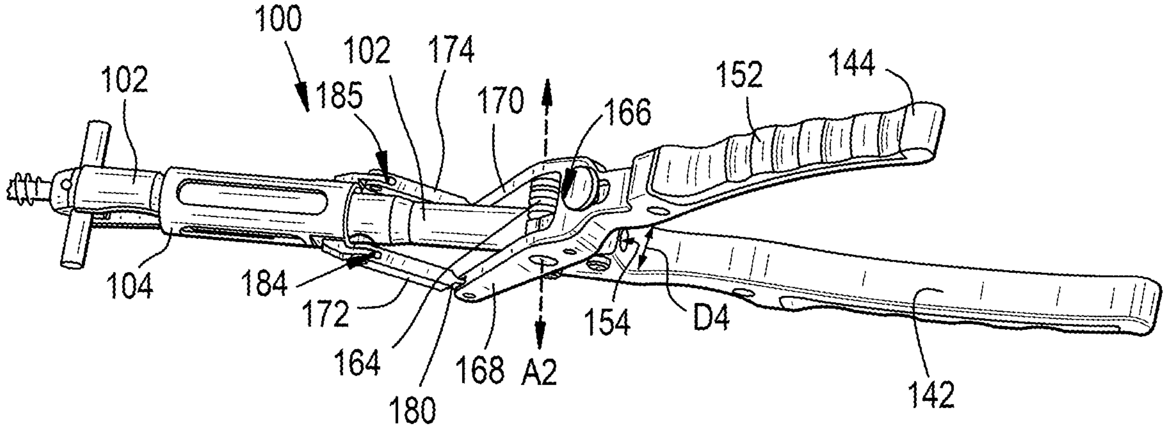
FIG. 4B is a top perspective view of the instrument of FIG. 4A.
Figure 4C:
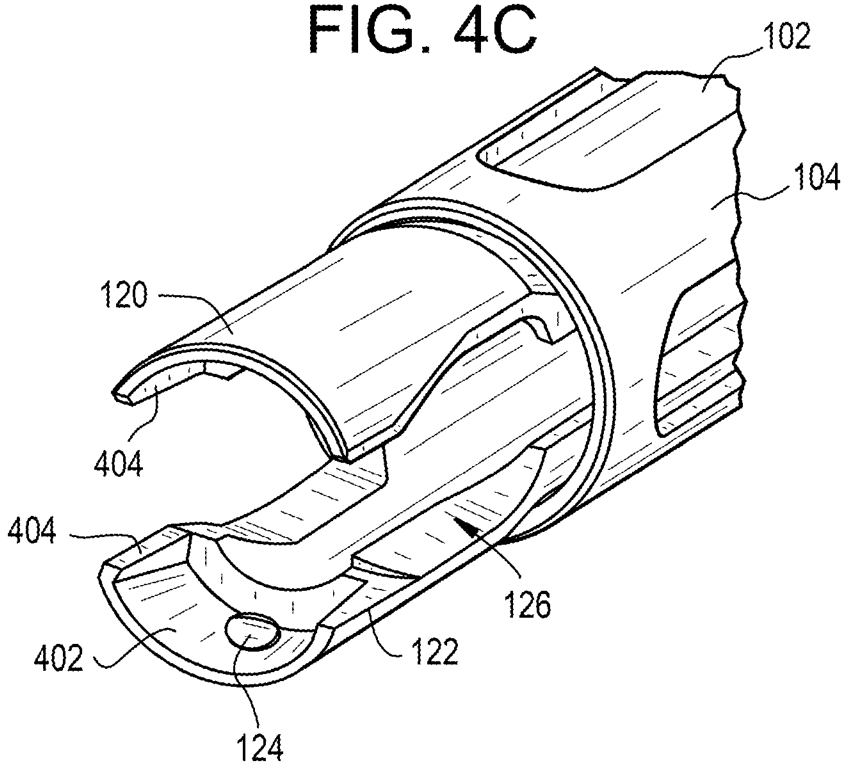
FIG. 4C is a detail view of a distal portion of the instrument of FIG. 4A.
Figure 4D:
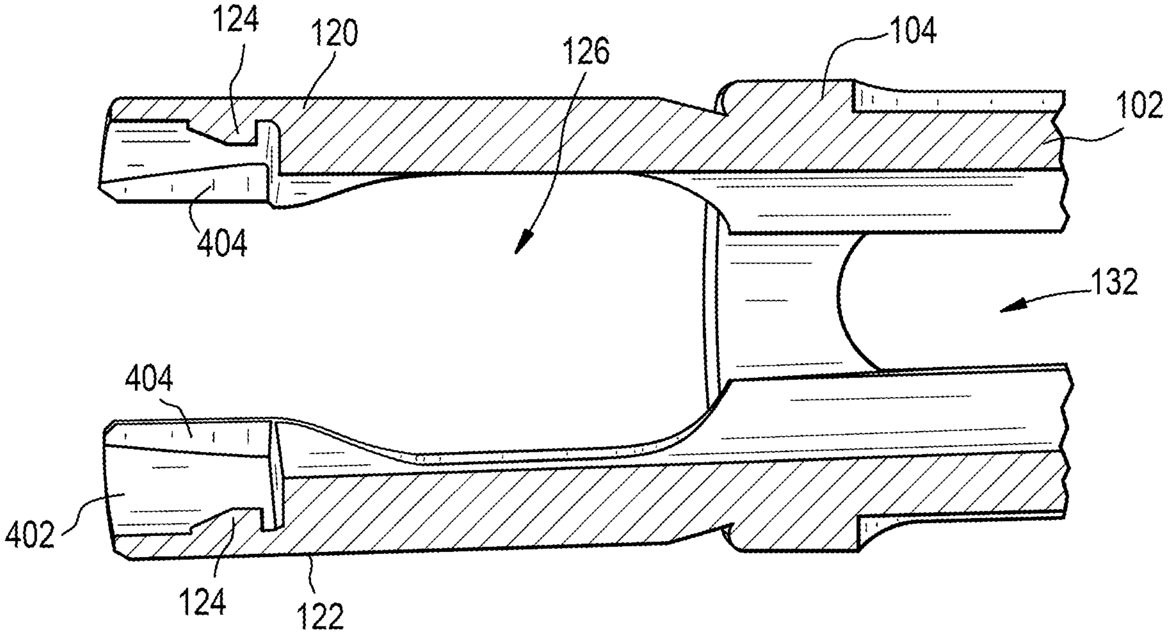
FIG. 4D is a detail longitudinal cross-sectional view of the distal portion of the instrument of FIG. 4A.

FIGS. 4C and 4D illustrate a distal portion of the instrument 100 in greater detail, including the mating elements 124. The mating element 124 can be a protrusion, such as a pin, nub, or a ridge extending across a width of the arm, that can be configured to be received within a slot or other recess formed in a proximal outer surface portion of a bone anchor receiver member to facilitate coupling between the components. In embodiments that include a ridge or other elongate protrusion, it can extend across an entire width of the arm or, in some embodiments, can extend across only a portion of a width of the arm or include one or more breaks along its length. Example bone anchors having such features are described in U.S. Pat. No. 7,179,261, the entire contents of which are incorporated by reference herein. Other engagement feature configurations are possible as well, including reversing the above-described configuration such that a protrusion formed on a bone anchor is received in a recess formed in the distal portion of the arms 120, 122.

In some embodiments, the mating element 124 can be disposed proximal to a distal-most end of the arm's distal portion and an inner surface of the arm distal to the engagement feature can be configured to facilitate alignment and coupling of the instrument with a bone anchor. For example, an internal surface 402 of the arm can have a shape or profile that is complementary to an outer surface of the bone anchor in order to facilitate coupling even in the event there is some amount of misalignment, whether that be, e.g., lateral or rotational misalignment along an axis of a rod, rotational misalignment along a longitudinal axis of the instrument 100, etc. In some embodiments, for example, the inner surface 402 can include a tapered profile complementary to an outer surface of opposed arms of a polyaxial bone anchor receiver head. In some instances, the inner surface 402 can include a conical tapering profile that is complementary to the conical tapering profile of a receiver member. Such an arrangement can allow for some pivoting misalignment between the receiver head and the instrument 100 that can be corrected as the instrument is advanced distally relative to the receiver head. In other embodiments, however, the profile can be flat without any tapering. Even in such a configuration, the additional extension of the distal portion of the arm beyond the engagement feature 402 can facilitate alignment and coupling between the instrument 100 and a bone anchor receiver member.

Further, the inner surface 402 can include sidewalls 404 extending outward from the inner surface 402 at lateral ends thereof. The sidewalls 404 can similarly include a tapering profile to aid alignment with a receiver member of a bone anchor, e.g., by self-correcting for rotational misalignment about the longitudinal axis of the instrument as the instrument is advanced distally relative to the bone anchor. In some embodiments, the opposed, inward-facing surfaces of each sidewall 404 can have a planar tapering profile that can be complementary to a planar tapering profile of abutting surfaces on a bone anchor receiver member. The various tapered surfaces can accommodate misalignment when coupling the instrument 100 to a bone anchor such that advancement of the instrument over the bone anchor forces the two components into proper alignment just prior to positive engagement of the arms 120, 122 with the anchor to simplify attachment of the instrument 100 to the anchor. As noted, the receiver member can include one or more complementary tapering profiles to the tapered surfaces provided on the outer sleeve. Further details on features of the anchor that can be utilized with the instruments disclosed herein can be found in U.S. Pat. Nos. 10,039,578 and 10,299,839, as well as U.S. Provisional Appl. No. 63/157,362, entitled "Multi-Feature Polyaxial Screw," and U.S. Provisional Appl. No. 63/157,395, entitled "Sequential Reducer and Modular Derotation Tube," both of which were filed on Mar. 5, 2021. The entire contents of each of these applications are incorporated by reference herein.

The rod slot 118 can be sized to receive the spinal rod 112 therethrough. For example, in some embodiments, the spinal rod 112 can be placed within the rod slot 118 at the proximal end 102*p* of the implant engagement member 102 and translated distally by the reduction member 104, as described below. The rod slot 118 can be sized to receive a spinal rod 112 of various diameters and, in some embodiments, the tapering width of the slot can allow for misalignment between the implant engagement member 102 and the bone anchor 110. As noted above, the rod slot 118 can taper proximally such that a distance between the arms 120, 122 at the distal end 102*d* is larger than a distance between the arms 120, 122 at a proximal portion of the slot. In some embodiments, the rod slot 118 can include an enlarged opening 126 along a distal portion of the implant engagement member 102 that is wider than the remainder of the rod slot 118 to further allow for situations in which the spinal rod 112 exhibits rotational and/or lateral misalignment about the longitudinal axis A1 relative to the rod-receiving head 116 and instrument 100 coupled thereto.

Figure 3:
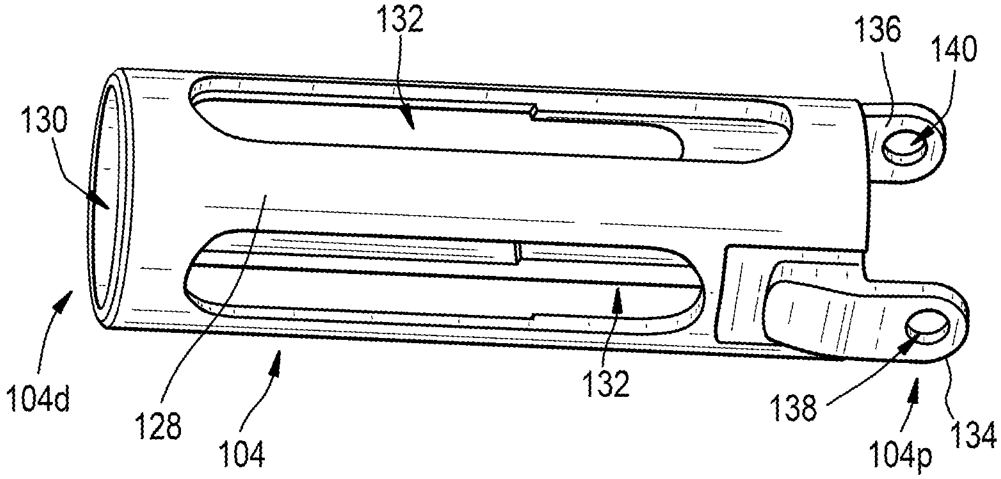
FIG. 3 is a perspective view of a reduction member of the reducer instrument of FIG. 1A.

Returning to FIG. 3, one embodiment of the reduction member 104 is illustrated. The reduction member 104 can be a reducer sleeve having a cylindrical sidewall 128 with a proximal end 104*p* and a distal end 104*d* that defines a channel or lumen 130 therebetween. The channel 130 can be configured to receive the implant engagement member 102 therethrough such that the reduction member 104 is disposed around the opposed arms 120, 122. As noted above, the distal end 104*d* of the reduction member 104 can be configured to abut against the rod 112 when it extends between the opposed arms 120, 122 of the implant engagement member 102. The reduction member 104 can have one or more openings 132 formed in the sidewall 128 thereof. One or more of the openings 132 can align with the slot 118 formed in the implant engagement member 102 to allow instrumentation and/or other devices to pass through the reduction member 104 and the implant engagement member 102 if necessary. In addition, the openings 132 can facilitate cleaning and sterilization of the device, permit visualization through the reduction member 104 during use to allow a surgeon to view the bone anchor, rod, closure mechanism, or other components or anatomy that might otherwise be blocked from view.

The proximal end 104*p* of the reduction member 104 can be coupled to the handle assembly 106 for axially translating the reduction member 104 proximally and/or distally with respect to the implant engagement member 102. For example, the reduction member 104 can include a pair of arms 134, 136 extending proximally therefrom. Each arm 134, 136 can include an opening 138, 140 for receiving a pin therethrough to enable pivotable coupling with other components.

FIGS. 4A-4D illustrate the instrument 100 in its initial, open position or unlocked configuration. In this configuration, the implant engagement member 102 can receive the bone anchor 110 between the arms 120, 122. The handle assembly 106 can be utilized to move the device 100 between the initial, unlocked position and a locked position or locked configuration. The handle assembly 106 can include a first handle 142 and a second handle 144 that are pivotably coupled to one another. As shown, the first handle 142 can be a stationary handle that remains substantially stationary while the second handle 144 pivots relative thereto, though it will be appreciated that, in some embodiments, the first handle 142 can pivot relative to the second handle 144, which is stationary, and/or the first and second arms can each move relative to one another. The first handle 142 can be pivotably coupled to the second handle 144 using a pivot pin 148 or a similar mating element inserted through a pair of openings (see FIGS. 5C-5D) formed in a housing 146 defined by the first arm 142. The pin 148 can extend through each of the openings along an axis A2 that is substantially transverse to the longitudinal axis A1.

The first handle 142 and the second handle 144 can each include a grip or grasping portion 150, 152 along a proximal portion thereof. For example, the grip portions 150, 152 can be positioned to facilitate grip of a hand of a user placed thereon. The grip portions 150, 152 can include features that assist in the comfort and ease of use of the instrument 100. Any number of features can be included to provide such comfort and ease of use. For example, the handles 142, 144 can include surface features to facilitate engagement, such as recesses or protrusions to engage with a user's fingers, finger loops, etc. In some embodiments, different materials can be utilized for form the grip portions 150, 152, or some portion thereof. For example, in some embodiments a silicone overmold or grip portion of a different material can be coupled to the handles 142, 144. The exploded view of FIG. 1C shows grip portions 150, 152 separated from the remainder of the handles 142, 144. It should be noted, however, that a user can grasp the handle 142, 144 itself directly, and in such cases the proximal portions of the handles can be the grip portions 150, 152.

A distal portion of the first handle 142 includes the housing 146 that includes a bore 154 configured to receive the proximal end of the implant engagement member 102. For example, a diameter D4 of the bore 154 can be larger than an outer diameter D3 of the implant engagement member 102 such that the implant engagement member 102 can be disposed within the bore 154. In this configuration, the lumen 117 of the implant engagement member 102 can be in communication with the bore 104 such that various devices and/or instruments, e.g., set screw inserters, etc., can be inserted therethrough to access the bone anchor 110.

The housing 146 of the first handle 142 can include a pair of prongs 158, 160 that extend from the housing to define a recess 162 therebetween, as shown in FIGS. 5A-5D. The pivot pin 148 can be received within an opening in each prong 158, 160 to mate the first handle 142 to the second handle 144. The openings in the prongs 158, 160 can align with corresponding openings in a distal portion of the second handle 144 such that the pivot pin 148 received therethrough can allow the second handle 144 to pivot relative to the first handle 142.

The instrument 100 can include a torsion spring 164 or another biasing element to bias proximal ends of the first and second handles 142, 144 away from one another. For example, the torsion spring 164 can be disposed around the pivot pin 148 to bias the handles 142, 144 toward the open configuration. As shown, the torsion spring 164 can be disposed around a portion of the pivot pin 148 within the recess 162 defined between the prongs 158, 160 to bias the first and second handles 142, 144 apart into the open position.

A distal portion of the second handle 144 can include a forked extension 166 having two arms 168, 170. The illustrated forked extension 166 of the second handle 144 begins at a mid-portion and extends distally. The arms 168, 170 of the forked extension can be spaced to receive the housing 146 of the first handle 142 and the reduction member 104 therebetween. As shown, the second handle 144 can also house the locking mechanism 108, as discussed further below.

Each of the arms 168, 170 of the forked extension 166 can be coupled to a linkage member 172, 174. As shown, the arms 166, 168 of the forked extension define recesses 176, 178 that can receive an extension 180 formed at one end of the linkage members 172, 174. Pins 182 can couple the components and allow pivoting between the distal end of the second handle 144 and the linkage members 172, 174. The linkage members 172, 174 can also define recesses 184, 185 on an opposite end thereof for coupling to the arms 134, 136 of the reduction member 104. For example, as shown, each arm 134, 136 of the reduction member 104 can be received in the recesses 184, 185 of the linkage members 172, 174. As noted above, pins 187 (see FIGS. 1C and 4A) can be received within the openings 138, 140 in the arms 134, 136 to couple the linkage members 172, 174 and allow pivoting of the linkage members 172, 174 relative to the reduction member 104.

Figure 6A:
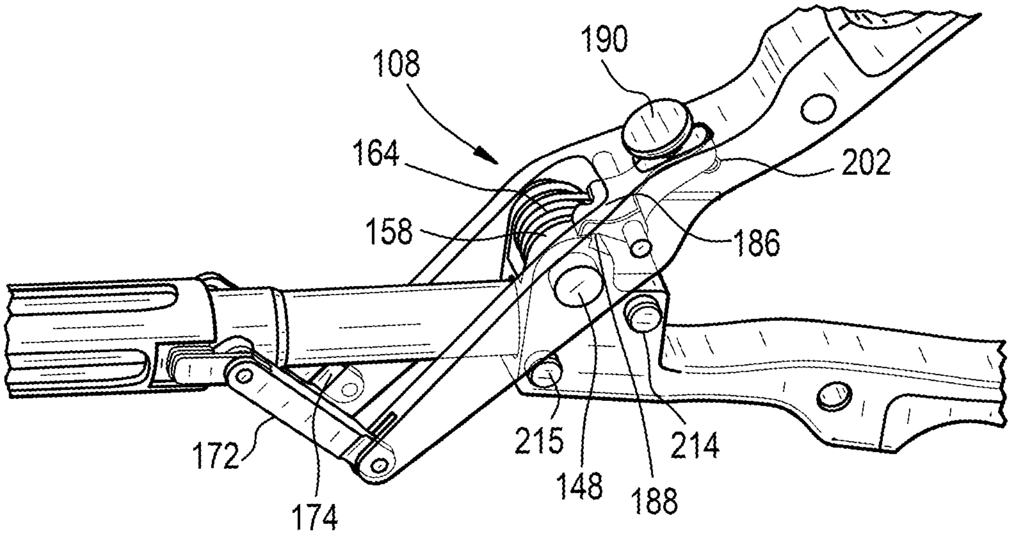
FIG. 6A is a partially-transparent perspective view of a locking mechanism of the instrument of FIG. 1A.
Figure 6B:
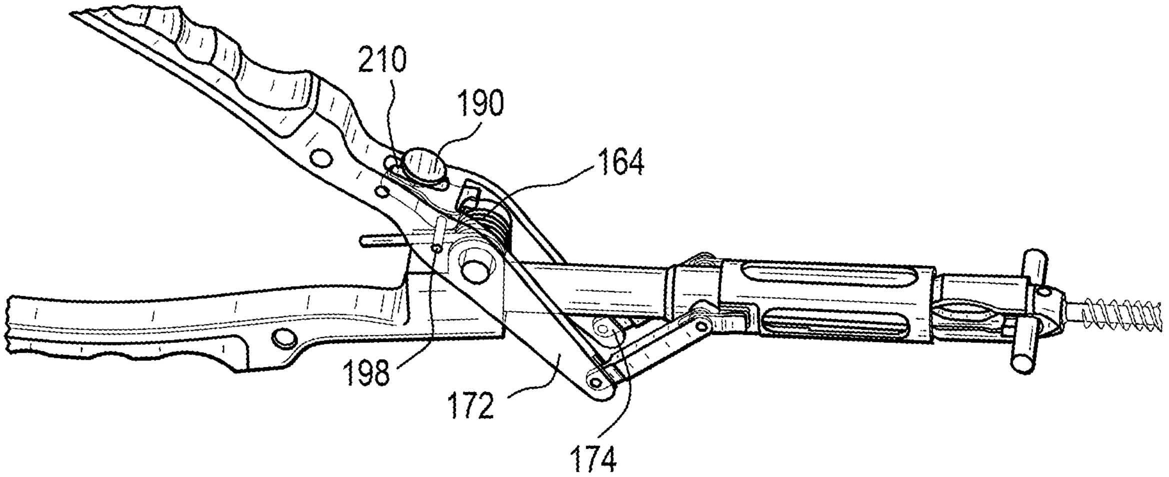
FIG. 6B is another partially-transparent perspective view of the locking mechanism of the instrument of FIG. 1A.

FIGS. 6A-6B illustrate the locking mechanism 108 of the instrument 100 in greater detail. The locking mechanism 108 can be located adjacent to the housing 146 of the first handle 142 distal to the proximal grip portion 150. Positioning the locking mechanism in this location can avoid the need for a locking mechanism near a proximal end of the handles that can interfere with a surgeon or other user's grasping the device, visualizing components or anatomy beyond the device, or introducing additional instrumentation through the device or adjacent thereto.

As shown, the locking mechanism 108 can include a pawl or latch 186 that locks the instrument 100 in the closed position or locked configuration. The pawl 186 can interact with a groove 188 formed in the housing 146 of the first handle 142 to lock the first and second handles 142, 144 against movement away from one another. As shown, the pawl 186 can be coupled to the second arm 144 while the groove 188 can be formed in the housing 146 of the first arm 142, though it will be appreciated that the location of the pawl 186 and the groove 188 can be reversed or otherwise modified. A button 190 can be coupled to and extend from the pawl 186 such that the button protrudes from an outer surface of the second handle 144 to facilitate user movement of the pawl. For example, the pawl 186 can be pivotably coupled to the second handle 144 with a distal end that is configured to seat within the groove 188 and a proximal end coupled to the button 190. To unlock the instrument 100, a user can depress the button 190, thereby causing the pawl 186 to pivot in a manner that draws the distal end of the pawl away from and clear of the groove 188. With the pawl 186 clear of the groove 188, the first and second handles 142, 144 can pivot such that proximal ends of the handles move away from one another. This can be accomplished manually by a user or via the bias force provided by the spring 164.

Figure 7A:
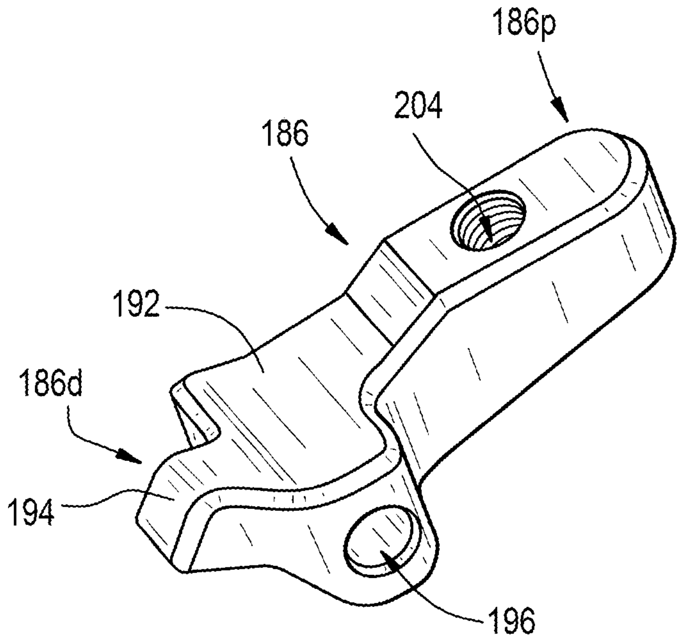
FIG. 7A is a detail perspective view of a pawl of the instrument of FIG. 1A.
Figure 7B:
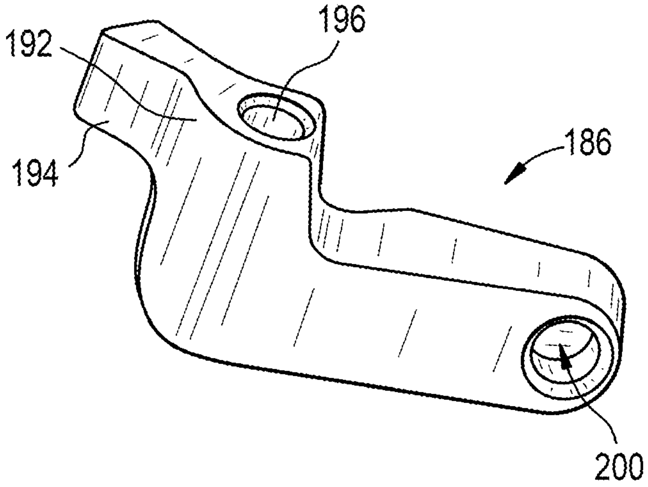
FIG. 7B is another detail perspective view of the pawl of the instrument of FIG. 1A.

FIGS. 7A-7B illustrate the pawl 186 in greater detail. As shown, the pawl 186 can include a body 192 having one or more extensions formed thereon. For example, the pawl 186 can include a distal extension 194 that is configured to engage the groove 188, as discussed above, to lock the orientation of the pawl 186 with respect to the first handle 142. The pawl 186 can include a series of bores formed therein. As shown, a transverse bore 196 can pass through the body 192 to couple the pawl 186 to the second arm 144. The transverse bore 196 can receive a pawl pin 198 therethrough for coupling the pawl 186 to the second handle 144 when the transverse bore 196 aligns with a corresponding opening in the second handle 144. Coupling of the pawl 186 with the second handle 144 is shown in FIGS. 1B, 5A, 5B, 6A, and 6B, among others.

A proximal end 186*p* of the pawl 186 can include a series of openings in the superior and inferior surfaces thereof. For example, a bore 200 in the inferior surface can be configured to receive a coil spring 202 therein. The spring 202 can abut an interior surface of the second handle 144 to bias the proximal end 186*p* of the pawl 186 away from the second handle 144 and urge a distal end 186*d* of the pawl toward the housing 146 of the first handle 142. This can cause the pawl 186 to ride along a surface of the housing 146 during actuation of the device and fall into the groove 188 when the pawl and groove are correctly aligned.

Figure 5A:
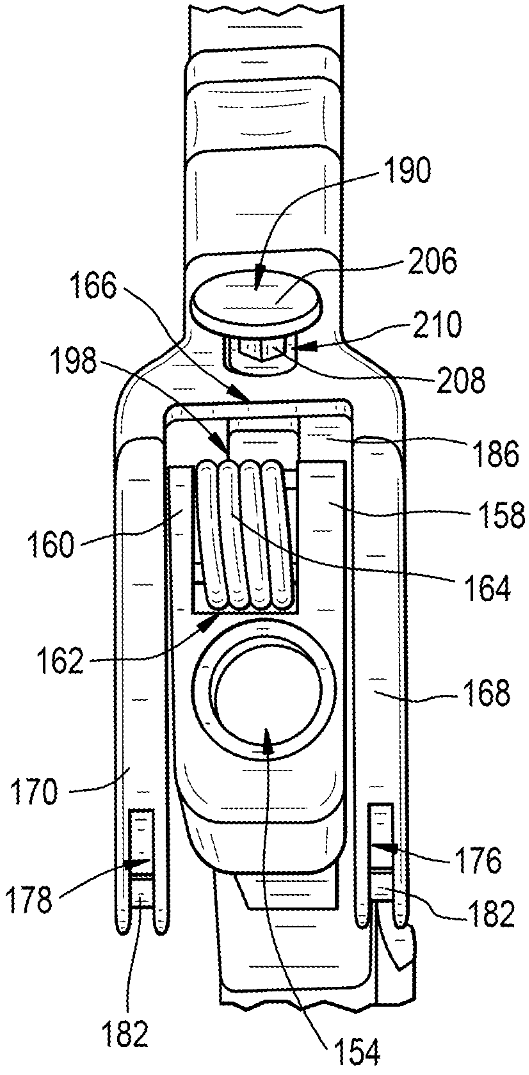
FIG. 5A is a front perspective view of first and second handles of the instrument of FIG. 4A.
Figure 5B:
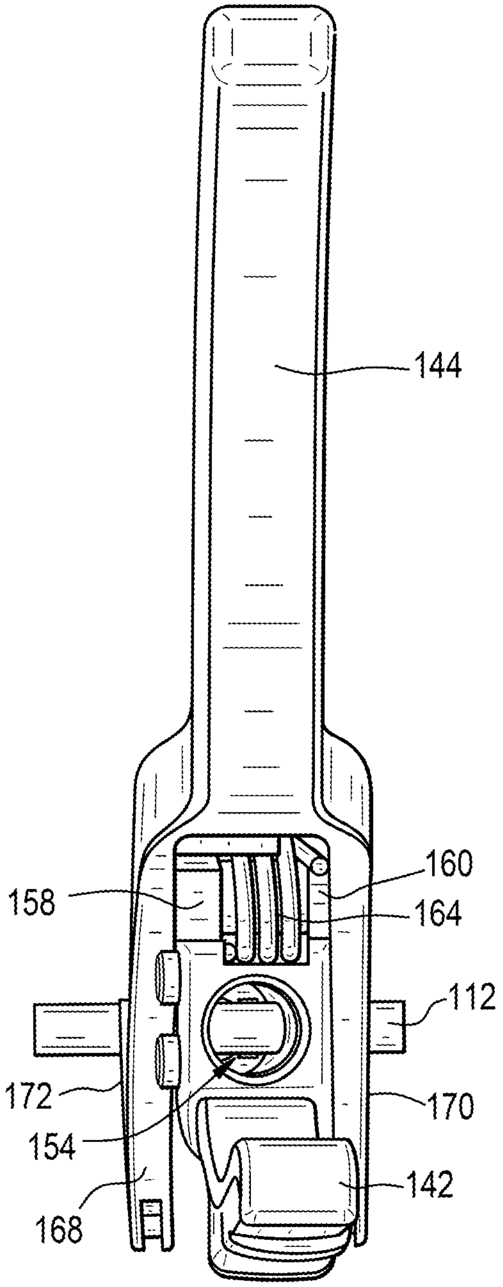
FIG. 5B is rear perspective view of first and second handles of the instrument of FIG. 4A.
Figure 5C:
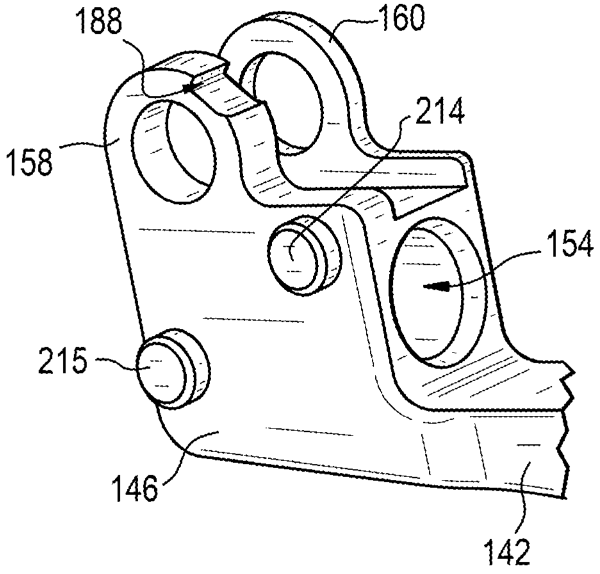
FIG. 5C is a detail perspective view of a distal portion of the first handle of the instrument of FIG. 4A.
Figure 5D:
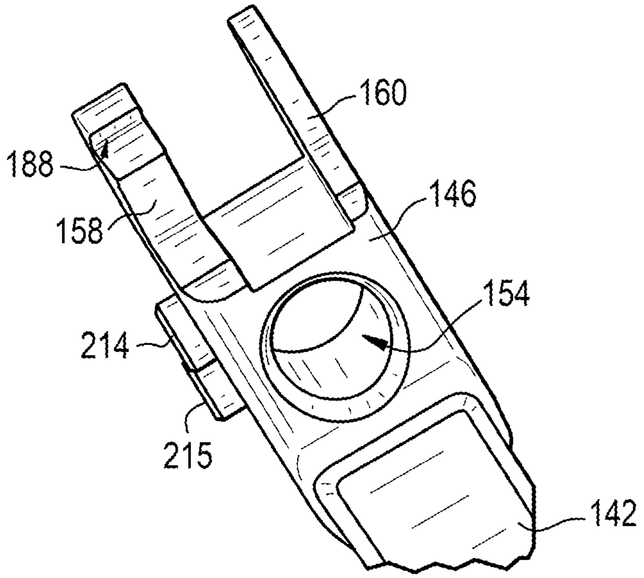
FIG. 5D is another detail perspective view of the distal portion of the first handle of the instrument of FIG. 4A.

The superior surface can include a threaded bore 204 for receiving the button 190. The button 190 can include a proximal head 206 and a threaded distal end 208 that threads into the threaded bore 204 such that the proximal head 206 extends above an outer surface of the second handle 144. The threaded bore 204 can align with a slot 210 formed in the second handle 144, as shown in FIG. 5A, such that the slot 210 is in communication with the threaded bore 204. Alignment between the slot 210 and the threaded bore 204 allows the proximal head 206 of the button 190 to extend through and out of the slot 210 to be pressed by a user during operation of the instrument 100. Moreover, the proximal head 206 can be larger than a size of the slot 210 to provide a large surface area for actuation of the button 190 during unlocking.

Returning to FIGS. 6A-6B, the instrument 100 is illustrated in the unlocked configuration. As shown, the implant engagement member 102 is disposed over the bone anchor 110 while the reduction member 104 is in a proximal position spaced from the bone anchor 110. The pawl 186 is resting on an outer surface of the prong 158 of the housing 146 of the first handle 142 distal to the groove 188. The linkage members 172, 174 are disposed at an oblique angle with respect to the longitudinal axis A1 of the instrument 100.

Figure 8:
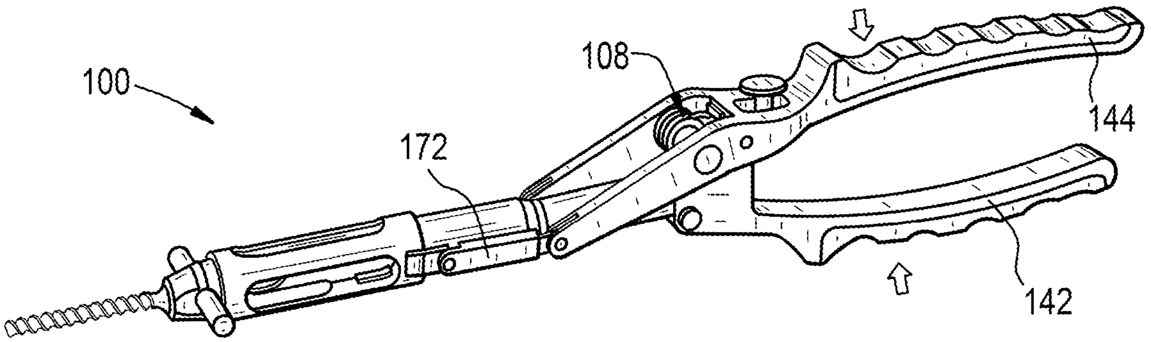
FIG. 8 is a perspective view of the instrument of FIG. 1A being actuated to move from an open position to a closed position.

FIG. 8 illustrates actuation of the instrument 100 to move from the open position to the closed position. Actuation of the instrument 100 includes exerting a force to move the first and second handles 142, 144 toward one another, e.g., by pivoting a proximal end of the second handle 144 toward the proximal end of the first handle 142. As noted above, in the illustrated embodiment, the second handle 144 functions as an actuator that can be moved toward the first handle 142. For example, as shown, the second handle 144 can rotate or pivot clockwise towards the second handle 144 in the view of FIG. 8 about the pivot pin 148. The application of force to the proximal portions of the handles 142, 144 to effect this movement can overcome the force from the spring 164 that urges the proximal ends of the arms away from one another. Such movement causes the distal portion 142*d* of the second handle 144 to move toward the longitudinal axis A1 such that the distal portion 142*d* of the second handle 144 extends closer to parallel to the implant engagement member 102. It will be appreciated that the distal portion 144*d* of the second handle 144 can, in some embodiments, cross beyond the longitudinal axis A1 depending on a shape thereof. Clockwise movement of the second arm 144 can move the distal extension 194 of the pawl 186 in tandem and clockwise along the outer surface of the prong 158 of the housing 146 of the first handle 142 toward—and ultimately into—the groove 188. In some embodiments, when the distal extension 194 enters the groove 188, the locking mechanism 108 is in the locked position and the reduction member 104 is in a distal position having reduced the spinal rod 112 into the receiving portion of the bone anchor 110. In some embodiments, when the pawl 186 enters the groove 188, the pawl can create an auditory and/or tactile indication such that a user can know they have achieved a desired level of spinal rod reduction, e.g., sufficient to introduce a set screw or other closure mechanism successfully. Engagement of the pawl 186 and groove 188 can be superior to, e.g., prior ratchet locking mechanisms because there is a one-step confirmation that the device 100 is in a locked position where set screw insertion or other implant locking/closure can be performed successfully. Prior ratchet locking mechanisms can require stepping through engagement with a plurality of ratchet teeth to reach a closed configuration where set screw insertion is possible. This can be time-consuming, provide inadequate feedback to a user (e.g., it can be unclear how many ratchet steps are needed to achieve desired reduction), can result in inadvertent locking of the ratchet mechanism prior to achieving desired reduction, etc.

Moving the first and second handles 142, 144 together can slide the reducer sleeve or reduction member 104 relative to the opposed arms of the implant engagement member 102. The reducer sleeve can contact the spinal rod 112 disposed between the opposed arms and urge it distally into the receiving portion of the bone anchor 110. For example, rotating the second arm 144 relative to the first arm 142 can pivot the linkage members 172, 174 from being obliquely angled with respect to the longitudinal axis A1 to being closer to parallel to the axis. In an example embodiment, pivoting the linkage members 172, 174 can move the reduction member 104 parallel to the longitudinal axis A1 to reduce the spinal rod 112 into the bone anchor 110. In particular, the reduction member 104 can be moved between a first position in which the reduction member 104 is either disengaged with the spinal rod 112 or is in contact with the rod at a location proximal to the bone anchor 110, and a second position in which the reduction member 104 is in contact with the spinal rod 112 and the rod 112 is disposed in the receiving portion of the bone screw 100.

Advancing the reducer sleeve 104 from the first position shown in FIG. 6B to the second position shown in FIG. 8 can also be effective to lock the opposed arms 120, 122 in a fixed position relative to the bone screw 100. This can secure the instrument 100 relative to the bone anchor 110 and ensure the two components do not become decoupled until a user desires and releases the pawl lock. In this sense, the instrument 100 can provide for simultaneous locking of the instrument relative to the bone anchor 110 and reduction of the spinal rod 112 into the receiving portion of the bone anchor via one actuation movement of the first and second handles 142, 144 toward one another. This can be advantageous in situations where the instrument 100 is used to repeatedly couple with various bone anchors implanted along a patient's spine and reduce a rod into each anchor. In such a situation, the ability to couple the instrument 100 with a bone anchor without needing to apply large axial forces, e.g., because the opposed arms 120, 122 are biased toward a relaxed position that easily receives a bone anchor therebetween, can be desirable. This configuration can also facilitate easier release of the instrument 100 from the bone anchor, as releasing the pawl lock and allowing the handles 142, 144 to move away from one another can result in moving the opposed arms 120, 122 away from one another in a manner that releases the instrument 100 from the bone anchor 110 and allows separation of the two components without the need for large axial forces.

Figure 9A:
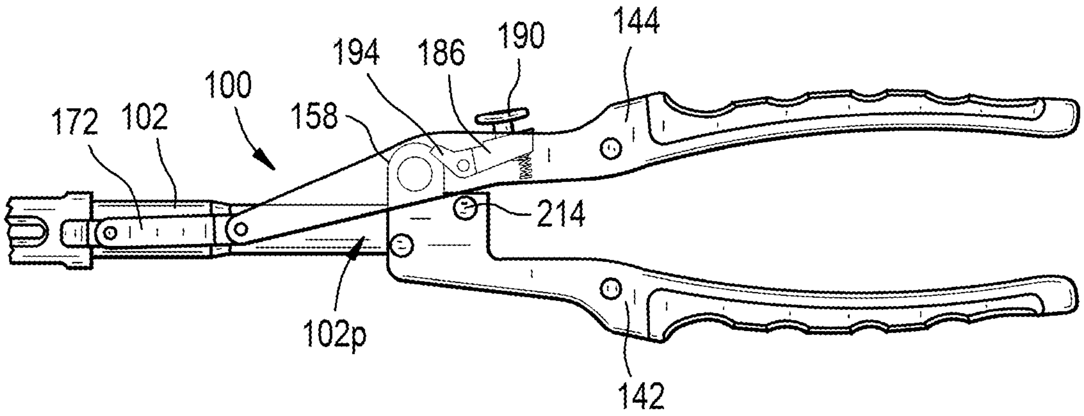
FIG. 9A is a partially-transparent perspective view of a locking mechanism of the instrument of FIG. 1A in a locked position.
Figure 9B:
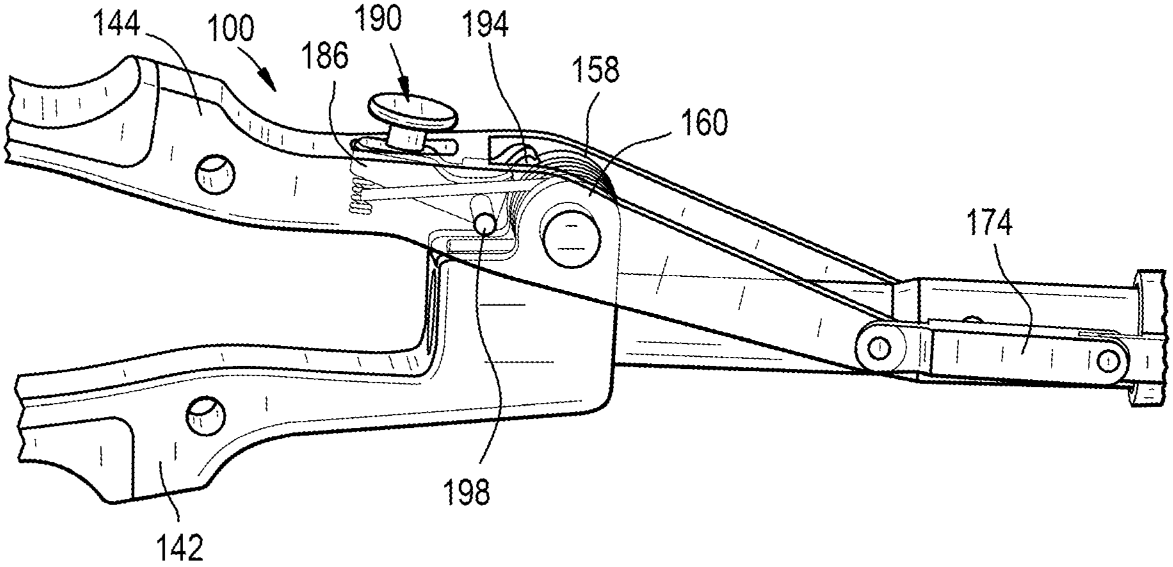
FIG. 9B is another partially-transparent perspective view of the locking mechanism of the instrument of FIG. 1A in a locked position.

FIGS. 9A-9B illustrate the locking mechanism 108 in the locked position. As shown, the distal extension 194 of the pawl 186 rests within the groove 188. In this locked configuration, the linkage members 172, 174 are pivoted into a position that is closer to parallel to the central longitudinal axis A1, while the reducer sleeve has been distally advanced along the opposed arms to reduce a spinal rod in contact with a distal end thereof.

Figure 10A:
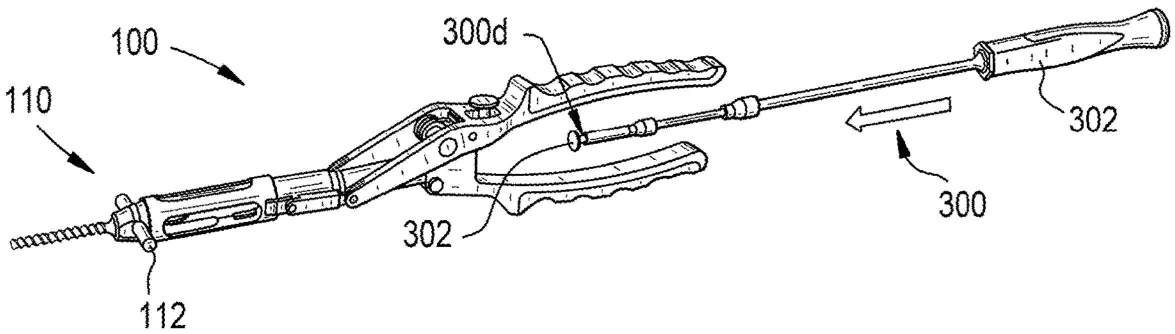
FIG. 10A is a perspective view of one embodiment of set screw insertion according to the present disclosure.
Figure 10B:
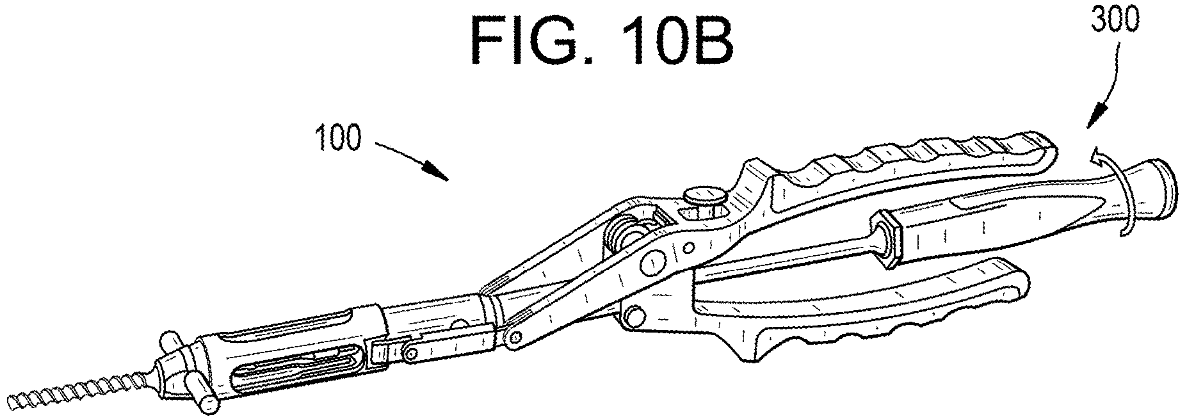
FIG. 10B is another perspective view of one embodiment of set screw insertion according to the present disclosure.
Figure 10C:
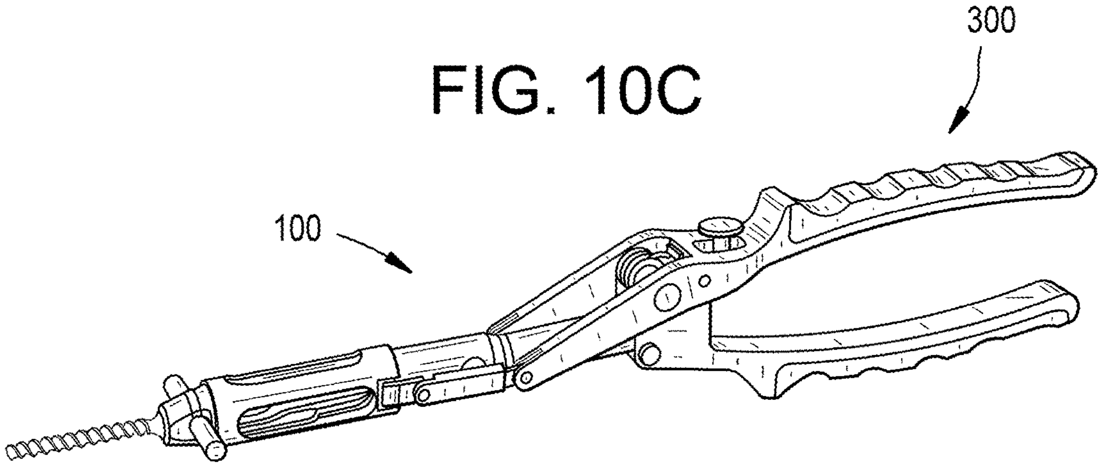
FIG. 10C is another perspective view of one embodiment of set screw insertion according to the present disclosure.

FIGS. 10A-10C illustrate an example embodiment of a set screw insertion procedure that can be used with the instrument 100 described herein. Set screws can be inserted into the bone anchor once the spinal rod has been sufficiently reduced such that a set screw can engage with threads formed on an interior proximal surface of the receiving portion of the bone anchor 110. A set screw inserter 300 having a set screw 302 disposed on a distal end 300*d* thereof can be introduced through the bore 154 in the instrument 100 for securing the set screw 302 to the bone anchor 110. As shown, the set screw inserter 300 can advance distally through the bore 154 in the housing 146 of the first handle 142 and the lumen 117 of the implant engagement member 102 until the set screw 102 is disposed within the rod-receiving head 116 of the bone anchor 110. Once the set screw inserter 300 is advanced to a position in which the set screw 302 engages with the rod-receiving head 116, a torque applied to a handle 304 of the set screw inserter 300 can tighten the set screw 302 to the rod-receiving head 116, as shown in FIG. 10B. The set screw inserter 300 can be rotated until the set screw 302 is sufficiently tightened to the bone anchor 110 to hold the reduced spinal rod 112 in place. Once sufficiently tightened, the set screw inserter 300 can be removed from the device 100, as shown in FIG. 10C.

In some embodiments, the instrument 100 can be configured to provide for the reduction of multiple diameter spinal fixation rods, e.g., 5.5 mm and 6 mm diameter rods, while providing sufficient reduction to allow a set screw or other locking element to engage a receiving portion of a bone anchor (e.g., threads of a set screw to engage with threads formed on a proximal surface of a bone anchor receiver member) and prevent excessive reduction that can create tension and inhibit easy decoupling of the instrument from the receiver member after the set screw or other locking element is installed.

Figure 11A:
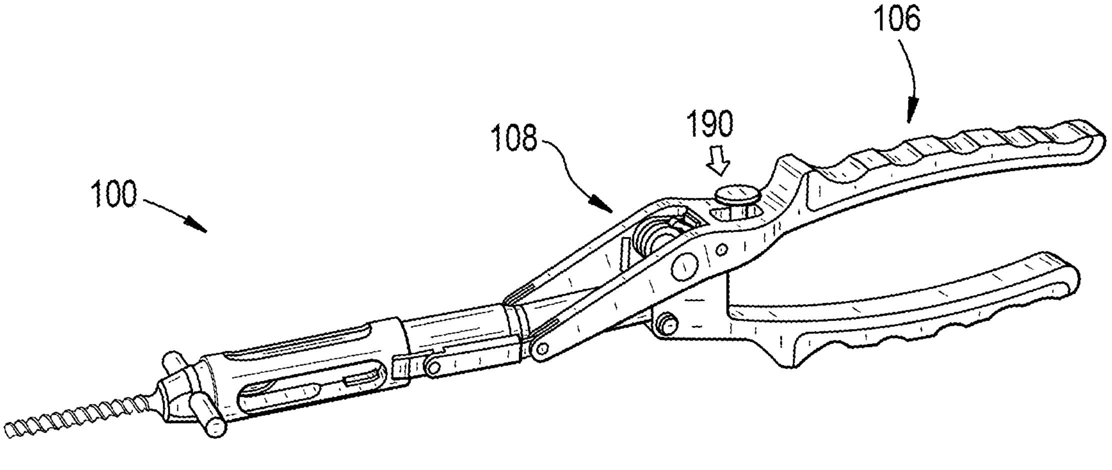
FIG. 11A is a perspective view of one embodiment of locking mechanism release according to the present disclosure.
Figure 11B:
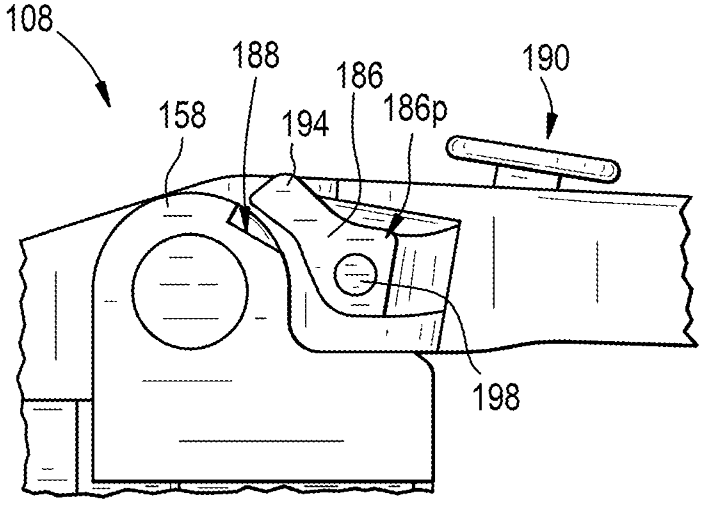
FIG. 11B is a detail cross-sectional view of locking mechanism release according to the present disclosure.
Figure 11C:
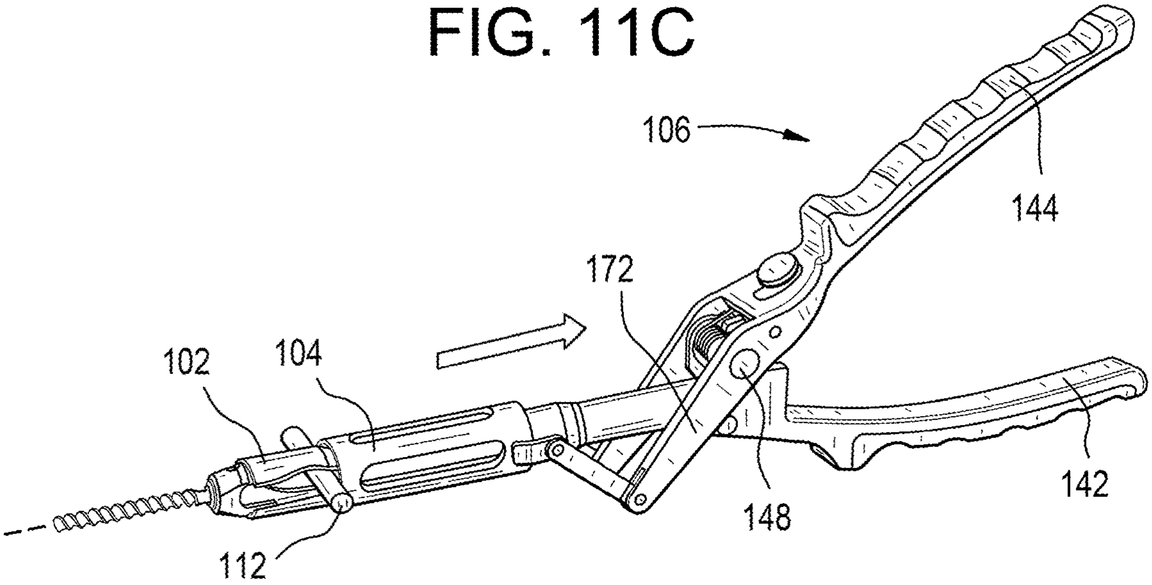
FIG. 11C is another perspective view of one embodiment of locking mechanism release according to the present disclosure.
Figure 11D:
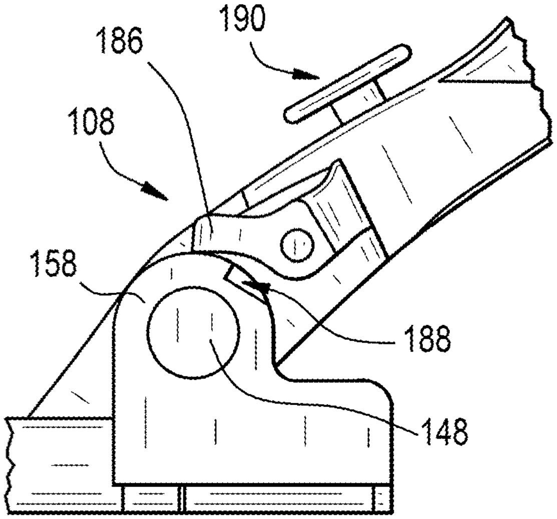
FIG. 11D is another detail cross-sectional view of locking mechanism release according to the present disclosure.
Figure 11E:
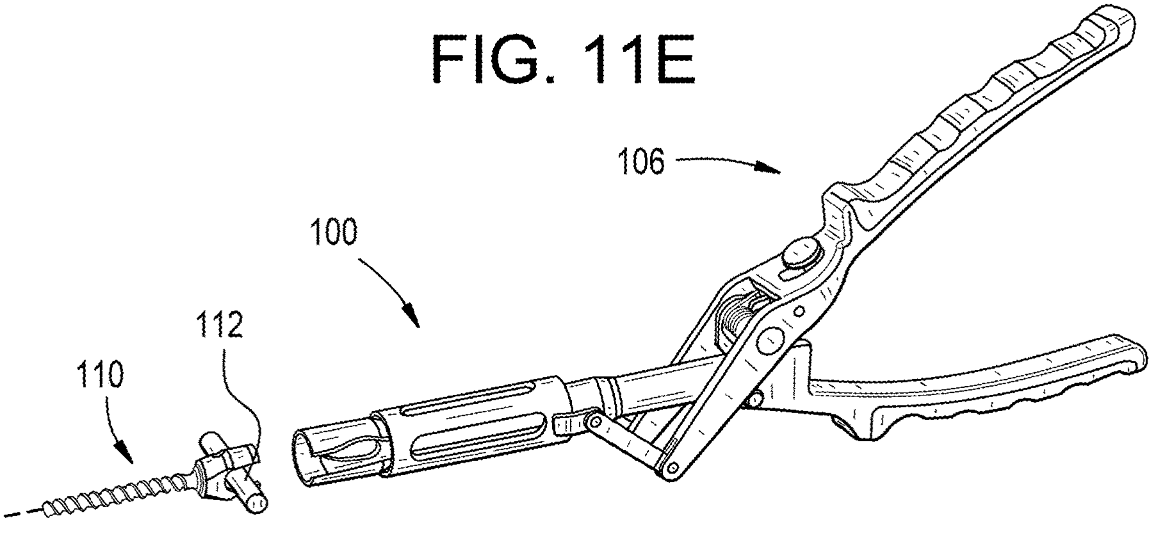
FIG. 11E is another perspective view of one embodiment of locking mechanism release according to the present disclosure.

FIGS. 11A-11E illustrate releasing of the locking mechanism 108 to move the instrument 100 from the locked position to the unlocked position. As shown, the button 190 can be pressed to unlock the instrument 100 by releasing the pawl 186 from the groove 188. For example, pressing the button 190 can exert a force onto the proximal end 186*p* of the pawl 186 to counter the force of the spring 202, thereby pivoting the pawl 186 about the pawl pin 198 to disengage the distal extension 194 from the groove 188 in the prong 158, as shown in FIG. 11B. Once the distal extension 194 is clear of the groove 188, the torsion spring 164 disposed in the joint region 146 can urge the handles 142, 144 apart. For example, the second handle 144 can rotate about the pivot pin 148 in a counterclockwise direction (in the view of FIG. 11B) away from the first handle 142. As shown, rotation of the second handle 144 can pivot the linkage members 172, 174 counterclockwise to move the reduction member 104 proximally relative to the implant engagement member 102 and out of the engagement with the spinal rod 112. The force exerted by the torsion spring 164 can cause the pawl 186 to rotate in a counterclockwise direction and slide distally along the prong 158 to return the locking mechanism 108 to its unlocked position, as shown in FIG. 11D. The instrument 100 can be proximally withdrawn from the bone anchor 110 leaving the reduced spinal rod 112 locked within the bone anchor by the set screw or other closure mechanism, as shown in FIG. 11E. The instrument 100 can then be coupled to another bone anchor for repeating the above-described procedure. Indeed, in some methods the reducer instruments disclosed herein are repeatedly utilized to reduce a rod into a plurality of bone anchors implanted along a patient's spine. The use of locking mechanism 108 in place of the prior long ratchet with multiple teeth disposed at a proximal end of the instrument can facilitate improved decoupling from the bone anchor, as prior ratchets can undesirably reengage during decoupling as the ratchet catch or pawl passes each successive ratchet tooth. Replacing the prior ratchet bar lock with the locking mechanism disclosed herein can eliminate this and promote easy-on and easy-off coupling and decoupling of the instrument 100 with the bone anchor.

In some embodiments, the first and second handles 142, 144 can be moved beyond a point at which the pawl 186 engages with the groove 188. As noted above, when the locking mechanism 108 enters the locked position, the pawl 186 can create an auditory and/or tactile indication that the spinal rod 112 has been reduced into the fastener. In some embodiments, the auditory and/or tactile indication can occur prior to the spinal rod 112 being fully reduced, e.g., into a bottom seating surface of the receiving portion of the bone anchor. The rod 112 need only be reduced far enough to allow a set screw to engage with threads formed at a proximal end of the bone anchor receiving portion. This can allow the set screw 302 to be inserted through the instrument 100 to perform final reduction and locking of the rod relative to the bone anchor. Such a configuration can reduce the tension present between the instrument and the bone anchor and facilitate easier decoupling of the instrument 100 from the bone anchor 110.

The instrument 100, however, can be actuated beyond the above-noted position where the pawl 186 sits within the groove 188. That is, a user can move the first and second handles 142, 144 closer to one another in a manner that urges the pawl 186 proximally away from the groove 188 and further advances the reducer sleeve 104 distally. A user can make use of this feature to, for example, release tension that may be on the pawl 186 and allow an easier release of the pawl 186 from the groove 188 when the button 190 is depressed. Alternatively or in addition, a user might utilize this feature to aid in set screw insertion and tightening to help reduce the rod a final degree with regard to the bone anchor.

Figure 12:
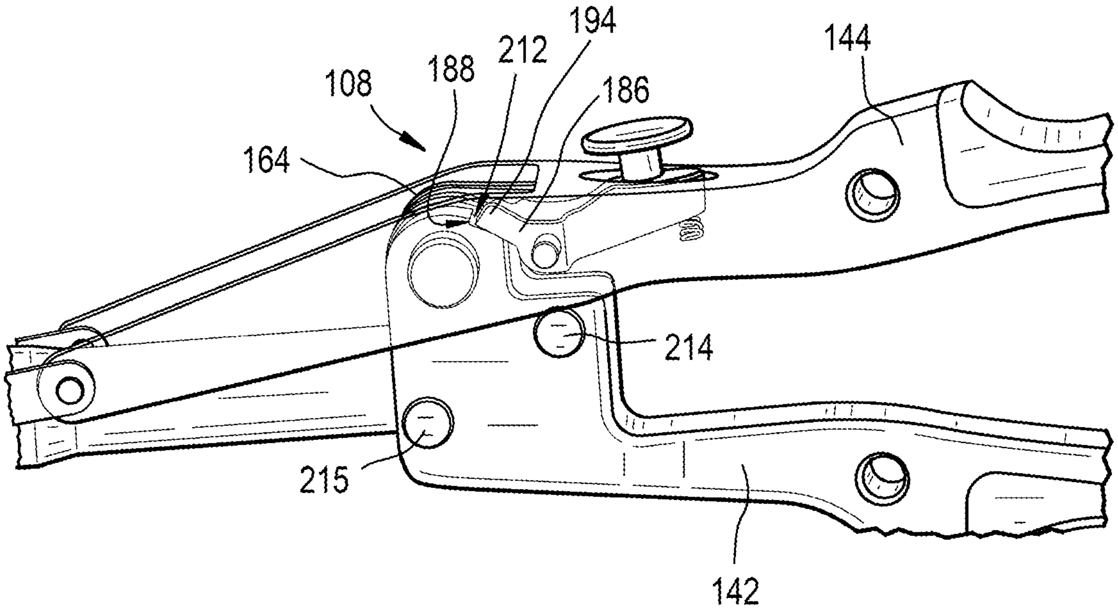
FIG. 12 is a partially-transparent detail view of the locking mechanism of the instrument of FIG. 1A during a further reduction actuation.

FIG. 12 illustrates an example embodiment of such a configuration where force is exerted onto the first and second handles 142, 144 to move them past the point in which the distal extension 194 of the pawl 186 falls into the groove 188. In this configuration, the distance between the arms 142, 144 is smaller than in the above-described closed position, with the distal extension 194 of the pawl 186 continuing to travel clockwise around the prong 158 of the housing 146 such that a gap 212 forms between the distal extension 194 and a wall of the groove 188. The additional movement of the handles 142, 144 in this configuration can push the reduction member 104 distally to further reduce the rod 112 into the bone anchor 100, as noted above. Rotation of the handles 142, 144 can continue until the reduction member 104 cannot translate further with respect to the implant engagement member 102 and/or when an ancillary stop for preventing further movement of the handles 142, 144 relative to one another is reached. For example, in some embodiments the housing 146 can include one or more protrusions formed thereon that can be configured to interfere with the second handle 144 and prevent further movement therebetween in a given direction. For example, the housing 146 can include a first protrusion or stop 214 formed thereon that can contact and interfere with the second handle 144 at a fully advanced position (as shown in FIG. 12) and prevent any further movement of the second handle 144 toward the first handle 142. In some embodiments, the instrument 100 can include a further protrusion or stop 215 configured to contact and interfere with the second handle 144 at a fully retracted position (as shown in FIG. 4A) and prevent any further movement of the second handle 144 away from the first handle 142.

Figure 13:
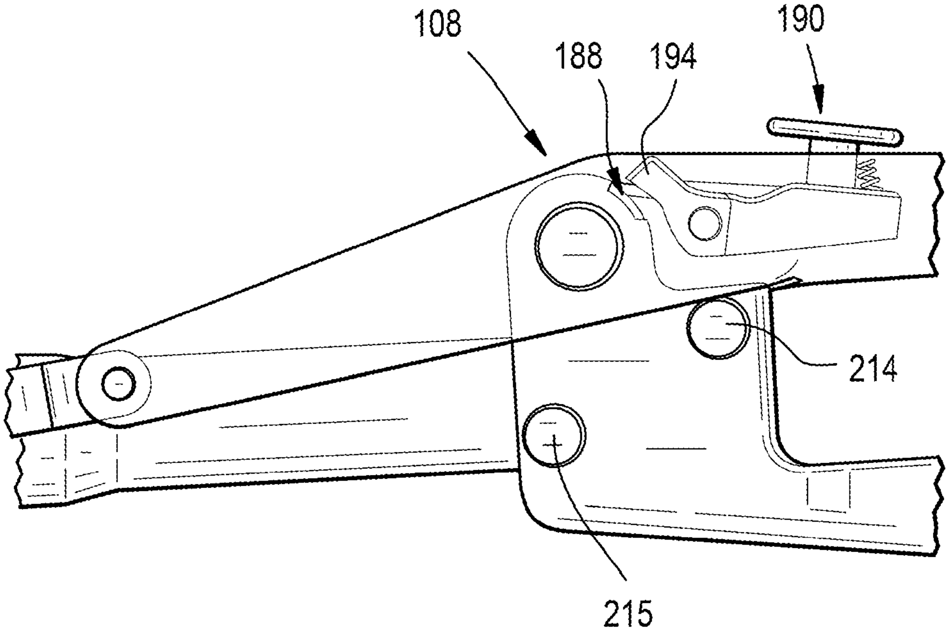
FIG. 13 is a partially-transparent detail view of the locking mechanism of the instrument of FIG. 1A during release.

FIG. 13 illustrates the locking mechanism 108 being released from the fully advanced configuration described above. Releasing the pawl 186 from this position is similar to the steps discussed with respect to FIGS. 11A-11E. As described above, actuating the button 190 can disengage the distal extension of the pawl from the outer surface of the housing to clear the groove 188, thereby allowing movement of the handles 142, 144 away from one another. As noted above, a user can move the instrument 100 to this fully advanced configuration in order to release any tension or force between the pawl 186 and groove 188 to facilitate easier release of the pawl via depression of the button 190.

Figure 14:
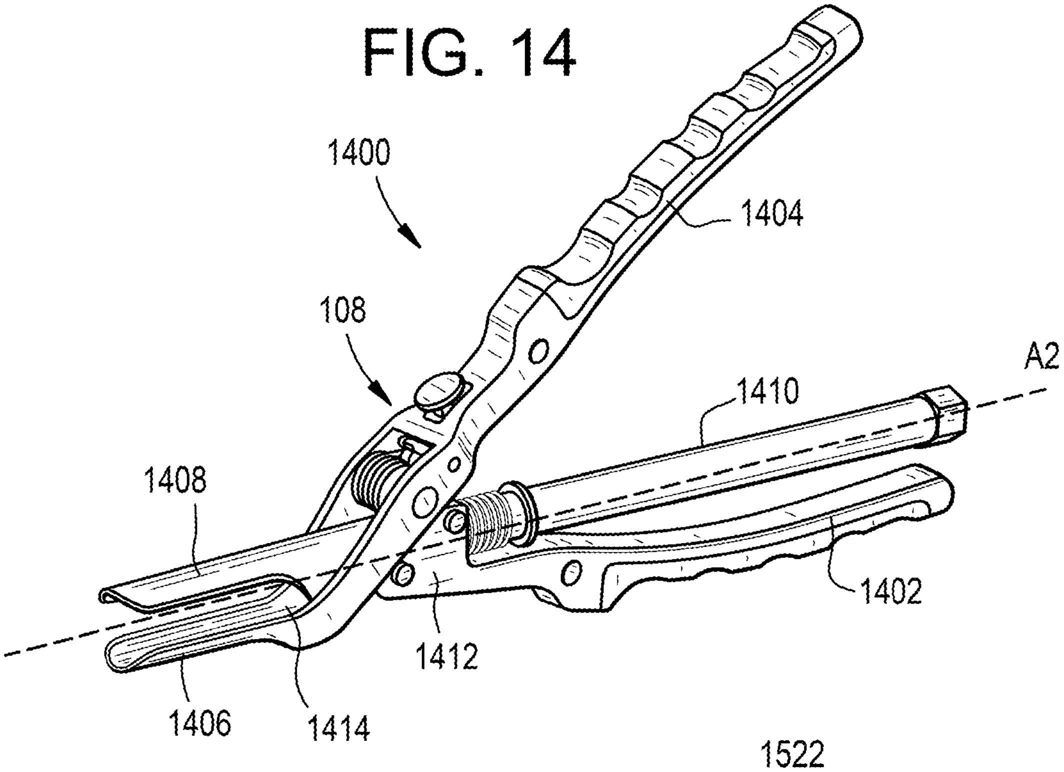
FIG. 14 is a perspective view of one embodiment of a reducer instrument according to the present disclosure.

FIG. 14 illustrates another embodiment of a reducer instrument 1400 according to the present disclosure. The instrument 1400 is a biplanar reducer configured to effect movement of a spinal rod in two dimension, e.g., axially along a longitudinal axis A2 of the instrument and laterally along an axis transverse to the longitudinal axis A2. This can be accomplished using first and second handles 1402, 1404 that include distally extending arms or jaws 1406, 1408 that can pivot toward or away from one another in combination with movement of the proximal portions of the handles toward or away from one another. Such movement can allow the capture of a rod between the distally extending arms 1406, 1408 and lateral reduction thereof as the arms move toward one another. Axial reduction can be accomplished utilizing a reducer tube 1410 having a threaded portion that is received within a threaded bore formed in a housing 1412 of the first handle 1402. A rod-engaging tip 1414 can be rotatably coupled to the reducer tube 1410 and extends into the space between the distally extending arms 1406, 1408. The rod-engaging tip 1414 can be translated distally without rotating as the reducer tube 1410 is rotated such that the threaded portion moves into the threaded bore of the housing 1412.

Figure 15A:
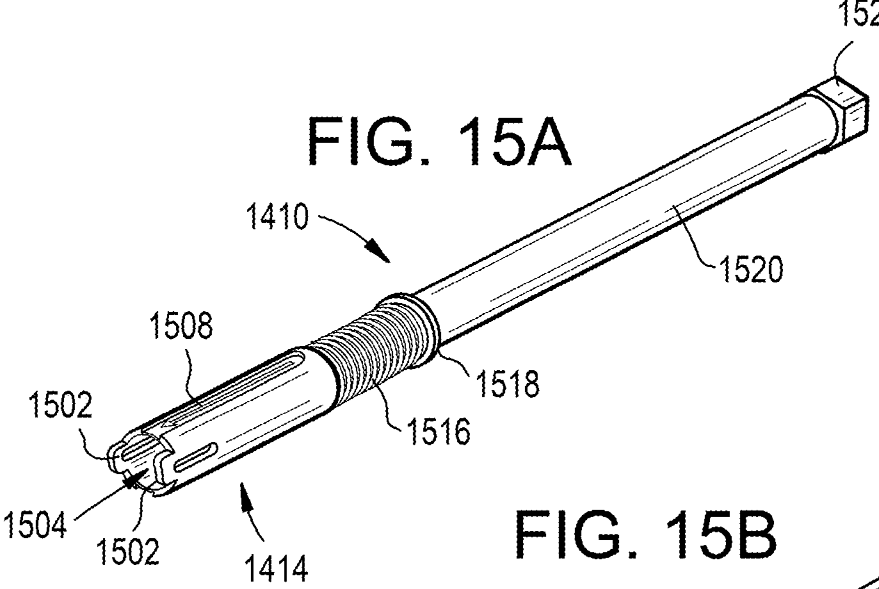
FIG. 15A is a perspective view of a reducer tube of the instrument of FIG. 14.
Figure 15B:
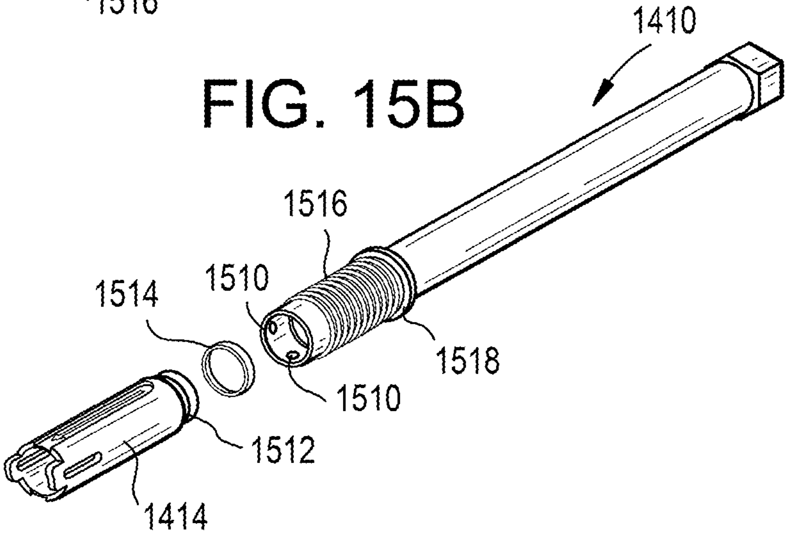
FIG. 15B is an exploded view of a reducer tube of the instrument of FIG. 15A.

FIGS. 15A and 15B illustrate additional views of the reducer tube 1410 and rod-engaging tip 1414. The reducer tube 1410 is rotatably coupled to the rod-engaging tip 1414, i.e., the two components can rotate relative to one another but are prevented from axially translating relative to one another. The rod-engaging tip 1414 can include opposed extensions 1502 formed at a distal end thereof that can be sized and shaped to contact a spinal fixation element, such as a rod, during an axial reduction maneuver. The extensions 1502 can also be configured to extend into a U-shaped gaps formed between opposed arms of a bone anchor receiver member, such that the rod-engaging tip 1502 can axially reduce a rod into the receiver member without interfering with delivery of a set screw or other locking element. Also to facilitate delivery of a set screw or other locking element, the rod-engaging tip 1414 and reducer tube 1410 can define an inner lumen 1504.

The rod-engaging tip 1414 can also include one or more openings 1506 formed in a sidewall to facilitate viewing into the lumen 1504. This can be useful to facilitate visualizing placement of a set screw or locking element delivered through the lumen 1504, as described in more detail below.

The rod-engaging tip 1414 can also include a groove 1508 or other recess formed in an outer surface thereof and extending at least partially along a length thereof. The groove 1508 can receive a protrusion formed on the surface of the bore of the housing 1412 in order to prevent relative axial rotation between the tip 1414 and the arms 1406, 1408.

As noted above, the reducer tube 1410 and rod-engaging tip 1414 can be rotatably coupled in a manner that permits relative rotation while preventing relative axial translation between the components. This can be accomplished using pins 1510 disposed through bores formed in the reducer tube 1410 and extending into an interior of the reducer tube. The pins can be received within a groove 1512 formed in a proximal end of the rod-engaging tip 1414. In addition, a thrust washer 1514 can be disposed between a proximal end of the rod-engaging tip 1414 and a shoulder formed on an interior surface of the reducer tube 1410.

The reducer tube 1410 can include a threaded outer surface portion 1516 configured to interface with threads formed on the surface of the bore of the housing 1412. A depth stop 1518 can be formed on the reducer tube 1410 at a position proximal to the threads 1516. The depth stop 1518 can be configured to contact a proximal portion of the housing 1412 in order to limit the distal advancement of the reducer tube 1410 and rod-engaging tip 1414 relative to the first and second arms 1406, 1408. This depth can be configured to allow for the reduction of multiple diameter spinal fixation rods, e.g., 5.5 mm and 6 mm diameter rods, while providing sufficient reduction to allow a set screw or other locking element to engage a receiver member (e.g., threads of a set screw to engage with threads formed on a proximal surface of a receiver member) and prevent excessive reduction that can create tension and inhibit easy decoupling of the instrument from the receiver member after the set screw or other locking element is installed. For example, in some embodiments the depth stop can be positioned to provide about 6.5 mm of clearance between a distal end of the rod-engaging tip 1414 and the base of a bone anchor receiver member rod slot at maximum axial reduction when the depth stop 1518 contacts the housing 1412. Such a configuration can allow using the device with both 5.5 mm and 6 mm rods with the benefits noted above. The depth stop 1518 can have a variety of forms, including any of a variety of protrusions formed on an outer surface of the reducer tube 1410 around part of or an entirety of its circumference. In the illustrated embodiment, the depth stop 1518 is a shoulder formed around a circumference (i.e., an entire perimeter) of the reducer tube 1410.

An intermediate portion 1520 can extend proximally from the depth stop 1518 to a drive feature 1522 formed on a proximal end of the reducer tube 1410. The intermediate portion 1520 can have a variety of shapes, diameters, and lengths. In the illustrated embodiment, the intermediate portion 1520 has a generally cylindrical shape. The drive feature 1522 formed at a proximal end of the reducer tube 1410 can allow for modular coupling of a driver handle, powered driver, or other torque application implement to the reducer tube 1410 in order to effect rotation of the tube and axial reduction of a spinal fixation element. The drive feature 1522 can also permit access to the lumen 1504 therethrough. The drive feature 1522 can have a variety of forms and sizes. In some embodiments, the drive feature 1522 can include one or more flats to facilitate the application of torque thereto. In the illustrated embodiment, the drive feature 1522 is a hex feature having six flat portions disposed around a circumference of the reducer tube 1410. Further, in the illustrated embodiment an outer diameter of the depth stop 1518 can be greater than an outer diameter of any other portion of the reducer tube 1410. Utilizing a lower profile drive feature 1522 can reduce the footprint of the instrument 1400 while still allowing a larger driver handle (e.g., a T-handle, powered driver, etc.) to be coupled to the instrument when needed.

The instrument 1400 can utilize a similar set of handles, housing, biasing element, and locking mechanism 108 as the instrument 100 described above. Accordingly, detail descriptions of these elements are not repeated here. The locking mechanisms described herein can provide the similar advantages to the instrument 1400. For example, a single actuation of the handles 1402, 1404 toward one another can simultaneously provide lateral reduction and secure coupling to a bone anchor and a user can be provided with clear feedback of sufficient lateral reduction and implant coupling when, e.g., the pawl falls into the groove of the locking mechanism. Subsequent rotation of the reducer tube 1410 can then effect axial reduction and a similar set screw inserter can be inserted through the reducer tube 1410 to deliver a set screw or other closure mechanism to the implant for final reduction and locking. Further details on biplanar forceps reducers that can be utilized in connection with the features described in the present disclosure can be found in U.S. application Ser. No. 17/522,164, entitled “Biplanar Forceps Reducers and Methods of Use,” filed Nov. 9, 2021. The entire contents of this application are incorporated by reference herein.

FIGS. 16-38 illustrate another embodiment of a reducer instrument 1600 according to the present disclosure. The instrument 1600 can be similar to the instrument 100 discussed above, except as explained in further detail below. For example, the instrument 1600 can include an alternative embodiment of an implant engagement member 1602 and a reduction member 1604. The proximal portion of the instrument 1600, however, can be the same as the instrument 100.

Figure 17:
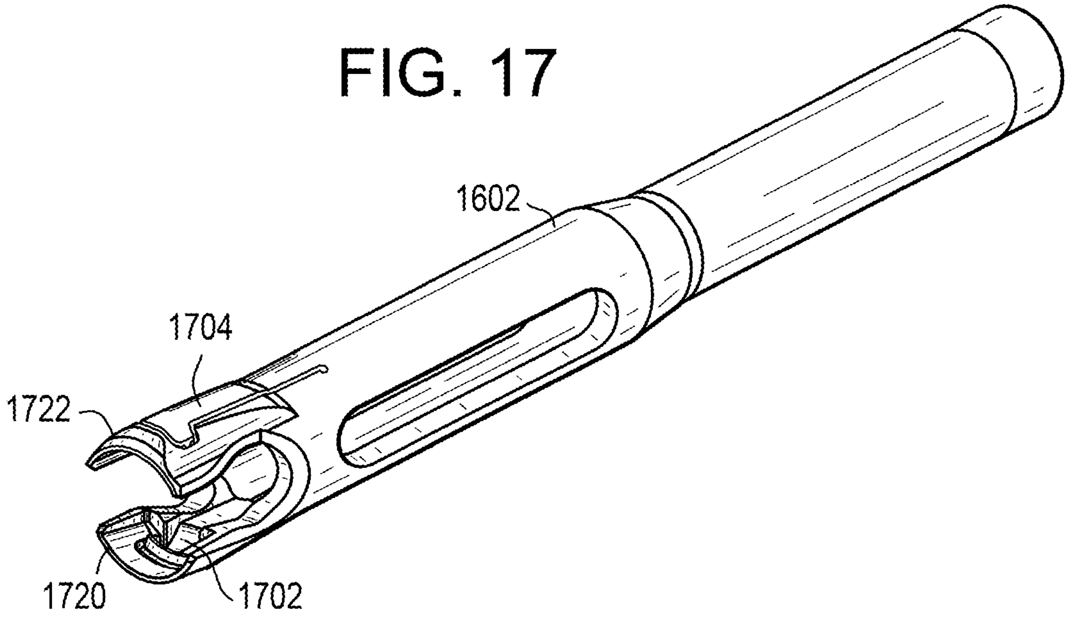
FIG. 17 is a perspective view of an implant engagement member of the instrument of FIG. 16.
Figure 18:
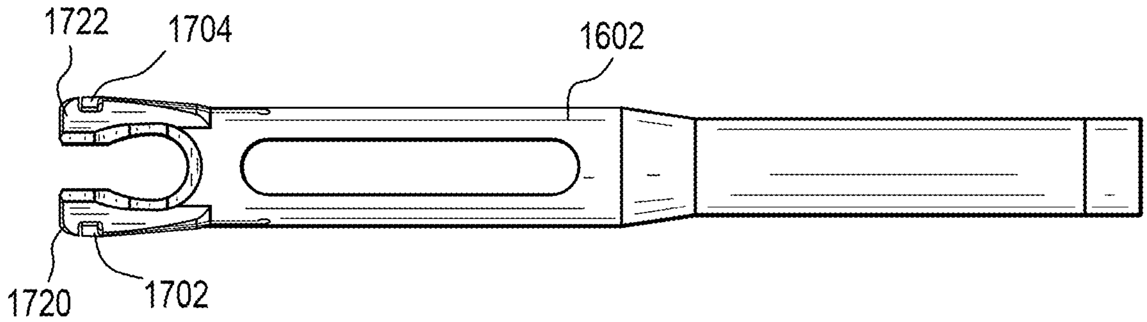
FIG. 18 is a side perspective view of the implant engagement member of the instrument of FIG. 16.
Figure 19:
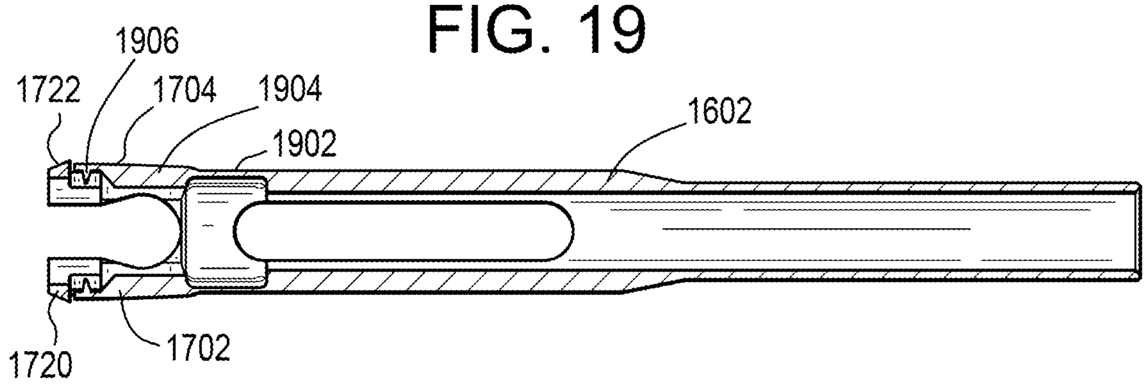
FIG. 19 is a side longitudinal cross-sectional view of the implant engagement member of the instrument of FIG. 16.
Figure 20:
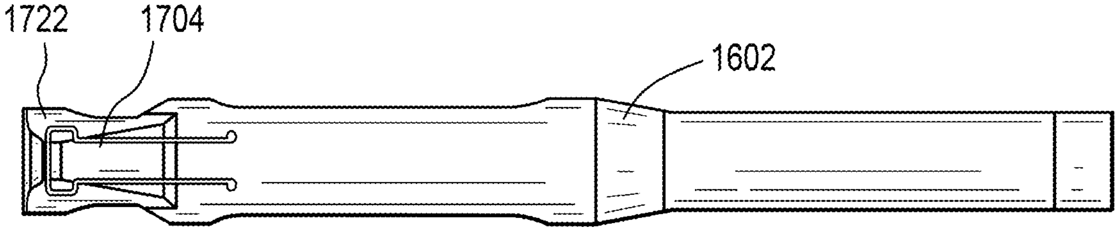
FIG. 20 is a top perspective view of the implant engagement member of the instrument of FIG. 16.
Figure 21:
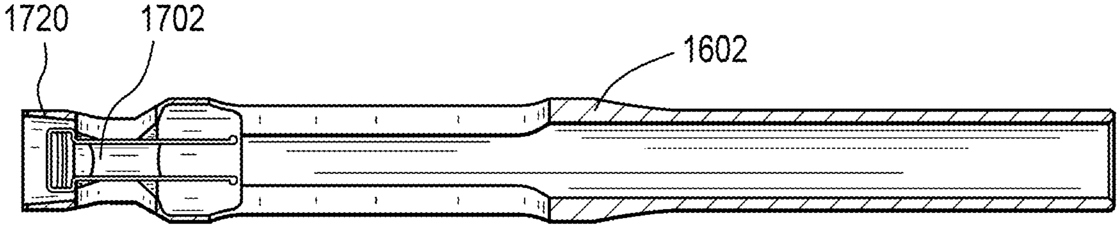
FIG. 21 is a top longitudinal cross-sectional view of the implant engagement member of the instrument of FIG. 16.

FIG. 17 illustrates the implant engagement member 1602 in greater detail. The implant engagement member 1602 can be similar to the earlier described implant engagement member 102 in certain respects, but also can have notable differences in the manner in which it is configured to engage an implant. For example, the implant engagement member 1602 can have opposed arms 1720, 1722 that are rigidly positioned relative to one another and do not flex toward or away from one another, as with the arms 120, 122 described above. The spacing of the arms 1720, 1722 can be configured to allow passage of a rod-receiving head 116 therebetween, with various internal surfaces of the arms 1720, 1722 contacting counterpart surfaces of the rod-receiving head 116 in a manner similar to that described with respect to the inner surfaces 402 and 404 above.

Each of the opposed arms 1720, 1722, however, can include a movable portion 1702, 1704 formed therein and configured to selectively latch onto a portion of the rod-receiving head 116 and lock its position relative to the implant engagement member 1602. The movable portions 1702, 1704 can be formed in a variety of manners, including, in some embodiments, by forming a nested cantilevered spring arm with a living hinge coupling the movable portion of the arm to the more rigid portion of the arm. This can be accomplished in a number of manners, including, for example, by partially cutting free the spring arm portion such that natural elastic deformation of the material combines with the geometry of the cut to permit the desired range of motion. In other embodiments, however, the movable portions 1702 can be formed from separate components coupled to the implant engagement member 1602 in a variety of manners. For example, the nested spring arm movable portions and implant engagement member can be formed from a welded multi-piece assembly of component parts.

FIGS. 18-21 illustrate side and top perspective and longitudinal cross-sectional views of the implant engagement member 1602. These views illustrate that each movable portion 1702, 1704 includes a narrowed portion 1902 at a proximal end thereof to form the living hinge, a thickened portion distal thereto, and an inwardly-extending protrusion 1906 that can be configured to extend into a groove or other recess formed in an outer surface of the rod-receiving head 116 in order to couple to the head of the implant engagement member 1602.

Figure 22:
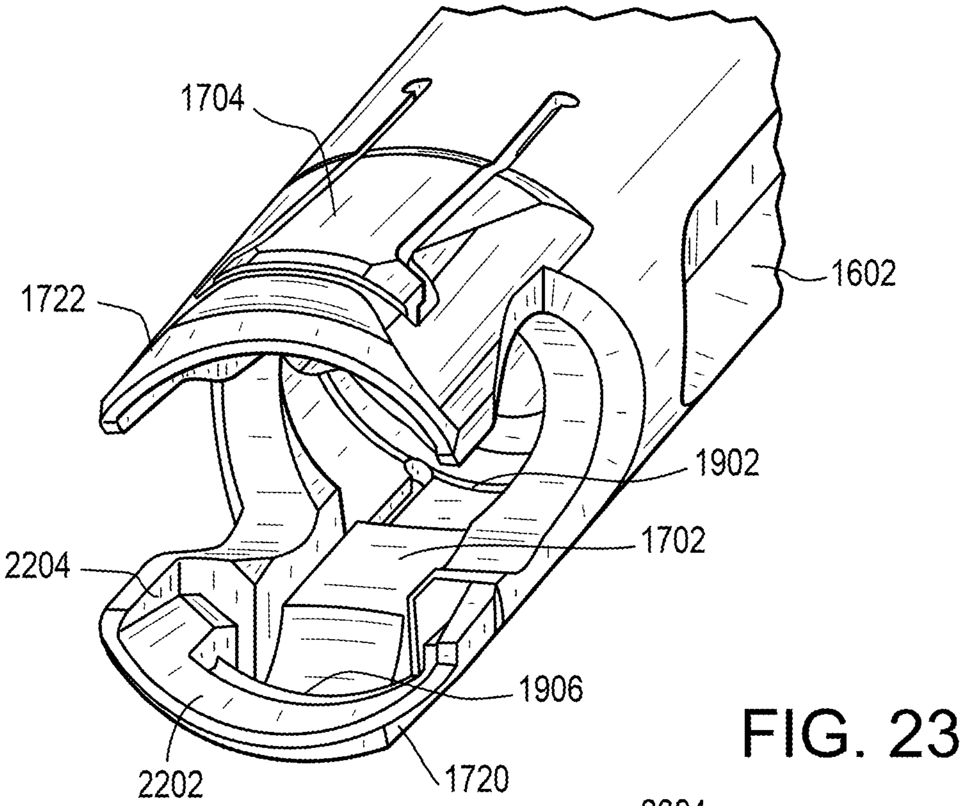
FIG. 22 is a detail perspective view of a distal portion of the implant engagement member of the instrument of FIG. 16.
Figure 23:
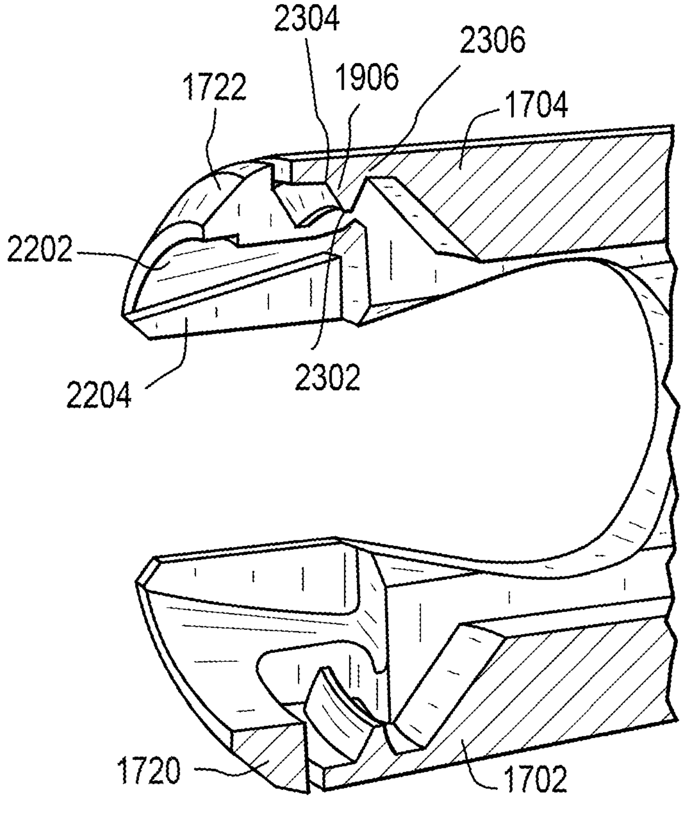
FIG. 23 is a side perspective longitudinal cross-sectional view of the implant engagement member of the instrument of FIG. 16.
Figure 24:
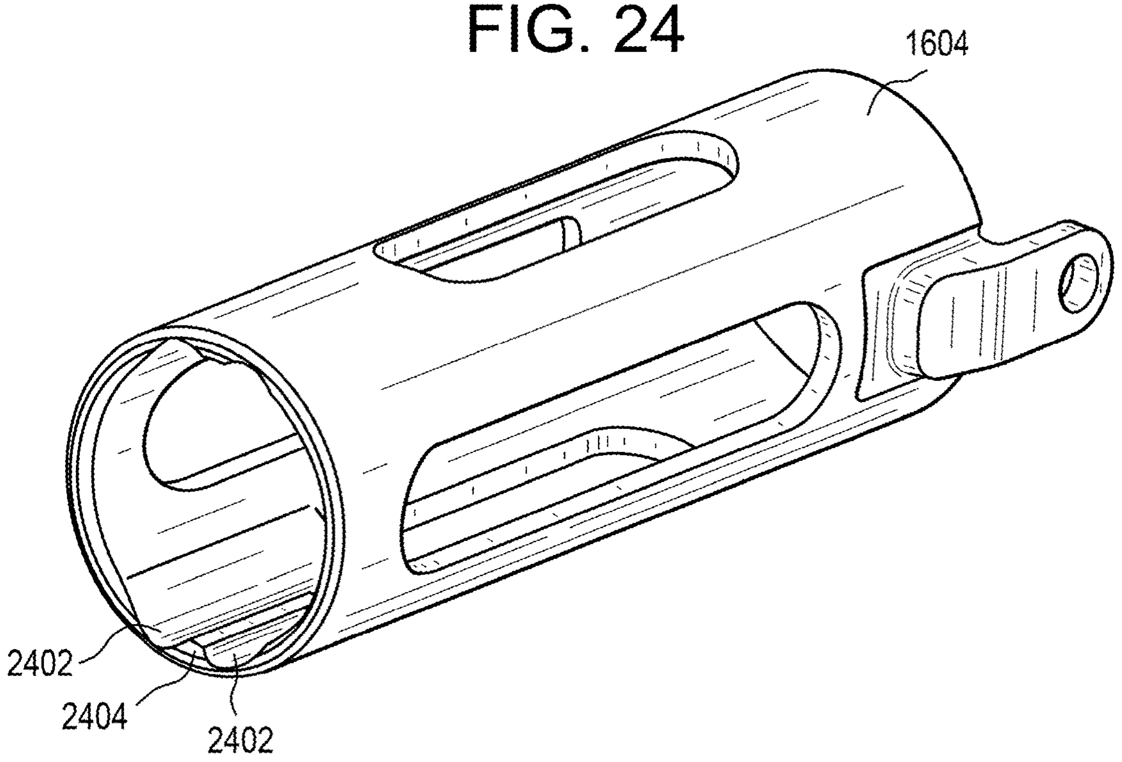
FIG. 24 is a perspective view of a reduction member of the instrument of FIG. 16.
Figure 25:
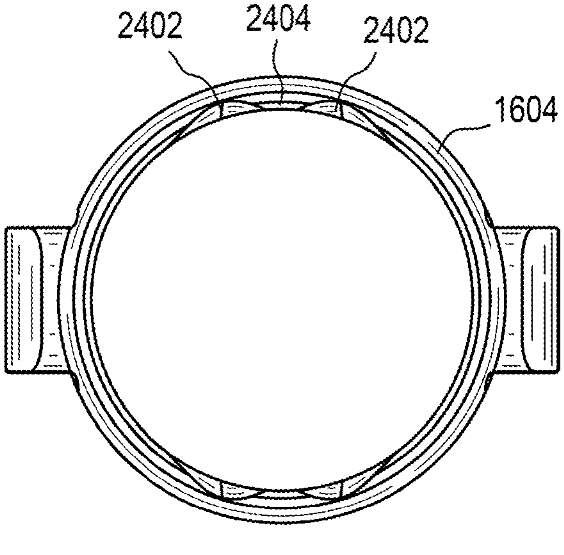
FIG. 25 is front view of the reduction member of the instrument of FIG. 16.

FIGS. 22 and 23 illustrate the distal end geometry of the implant engagement member 1602 in greater detail. As noted above, the opposed arms 1720, 1722 can include internal surfaces 2202 and 2204 that are similar to surfaces 402 and 404 described above and can be configured to interface with complementary-shaped and -dimensioned surfaces on a rod receiving head 116 to facilitate coupling the two components in a desired orientation and with a high degree of rigidity to prevent relative movement between the two components when coupled.

As can be seen in these figures and especially in the detail view of FIG. 23, a resting position of each movable portion 1702, 1704 is such that an outer surface thereof remains in alignment with an outer surface of the corresponding arm 1720, 1722 (e.g., the movable portion is not recessed below an outer surface defined by the arm and also does not protrude from such an outer surface). Similarly, on the interior side of each movable portion 1702, 1704, the projection 1906 has a resting position where it does not interfere with passage of a rod-receiving head 116 into or out of the space between the opposed arms 1720, 1722. In other words, to help retain a rod-receiving head 116 to the implant engagement member 1602, the movable portions 1702, 1704 must be moved radially inward from their resting positions, as explained in more detail below.

Another feature of the distal end geometry of the implant engagement member 1602 is that the rigid arms 1720, 1722 can serve as a guard to prevent any hard or soft tissue from interfering with the movement of the portions 1702, 1704. This can be an issue with certain reducers that utilize inwardly deflecting arms or other components to grasp an implant, such as a rod-receiving head 116. Tissue surrounding the instrument can interfere with the outward movement of the arms and the release of the instrument from the implant. With the illustrated instrument 1600, however, the movable portions 1702, 1704 have an outer surface aligned with the outer surface of the rigid implant engagement member arms 1720, 1722 when in an open or released state. This means the rigid arms 1720, 1722 can serve as a guard to maintain tissue spacing during use and a clear path for the inward and outward deflection of the movable portions 1702, 1704. This can ensure a more reliable latch and release of the instrument 1600 to the rod-receiving head 116.

To this end, in some embodiments the inwardly-extending protrusion 1906 of each movable portion 1702, 1704 can also be formed with a positive draft that does not include an undercut surface. In the embodiment of FIG. 23, for example, the protrusion 1906 is shown with a generally triangular cross-sectional shape where the apex 2302 of the triangle is disposed between the endpoints 2304, 2306 of its base. This can allow more reliable engagement and release of the protrusion with a groove or other recess formed in a rod-receiving head 116 and avoid binding of the components upon release, for example.

Figure 26:
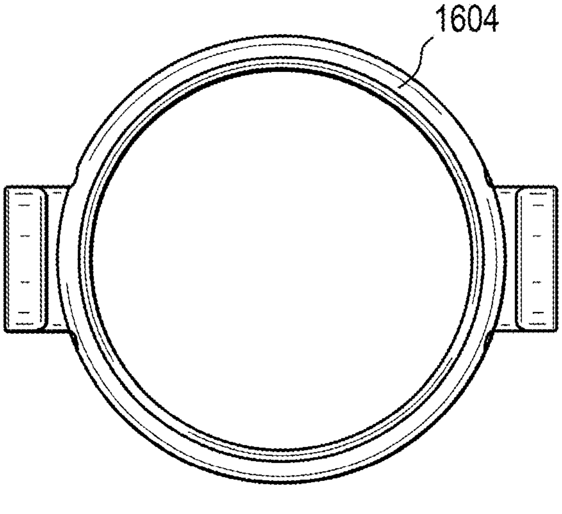
FIG. 26 is a rear view of the reduction member of the instrument of FIG. 16.
Figure 27:
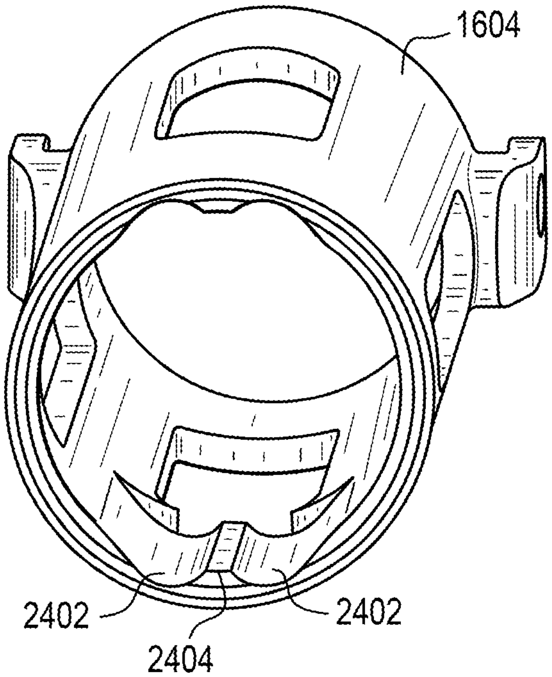
FIG. 27 is a front perspective view of the reduction member of the instrument of FIG. 16.
Figure 28:
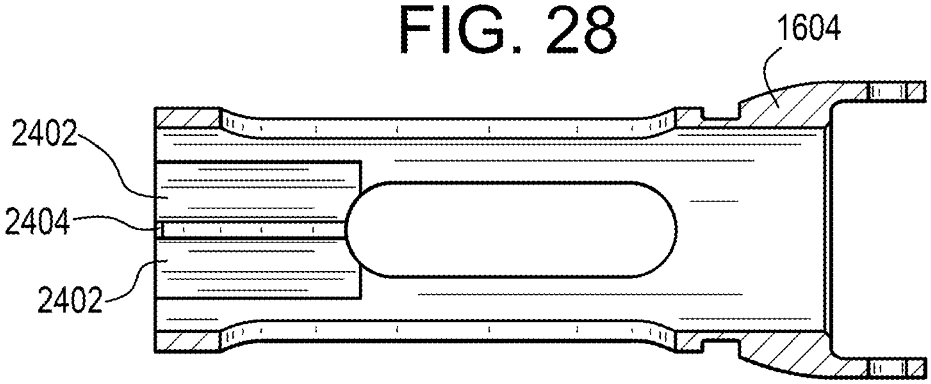
FIG. 28 is a top longitudinal cross-sectional view of the reduction member of the instrument of FIG. 16.
Figure 29:
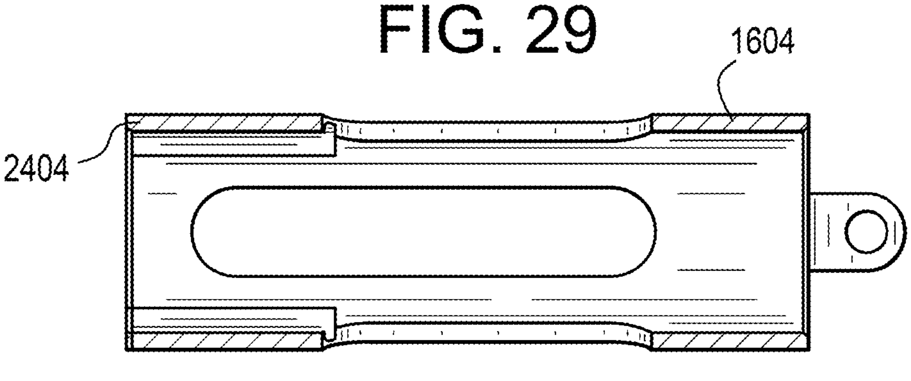
FIG. 29 is a side longitudinal cross-sectional view of the reduction member of the instrument of FIG. 16.

FIGS. 24-29 illustrate the reduction member 1604, which is similar to the reduction member 104 (e.g., the rear view of FIG. 26 is the same for each) but includes certain modifications to interface with the movable portions 1702, 1704 and control their actuation in the manner described above. In particular, a distal portion of the reduction member 1604 includes channels or recesses 2402 formed along an internal surface thereof extending proximally from the distal end. In the illustrated embodiment, two parallel channels 2402 extend to create a central ridge 2404 extending therebetween. The feature is repeated on opposite sides of the inner surface of the reduction member 1604 to align with the movable portions 1702, 1704 disposed on opposed arms 1720, 1722 of the implant engagement member 1602.

Figure 30:
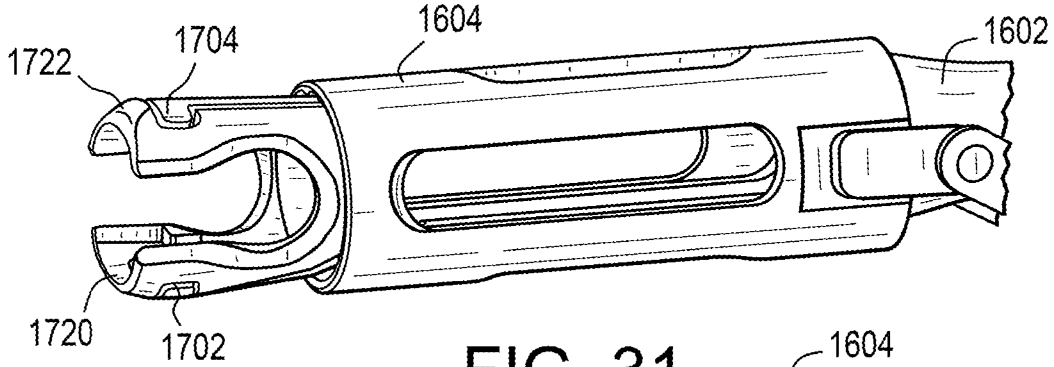
FIG. 30 is a perspective view of a distal portion of the instrument of FIG. 16A at a first, proximal-most position relative to the implant engagement member.
Figure 31:
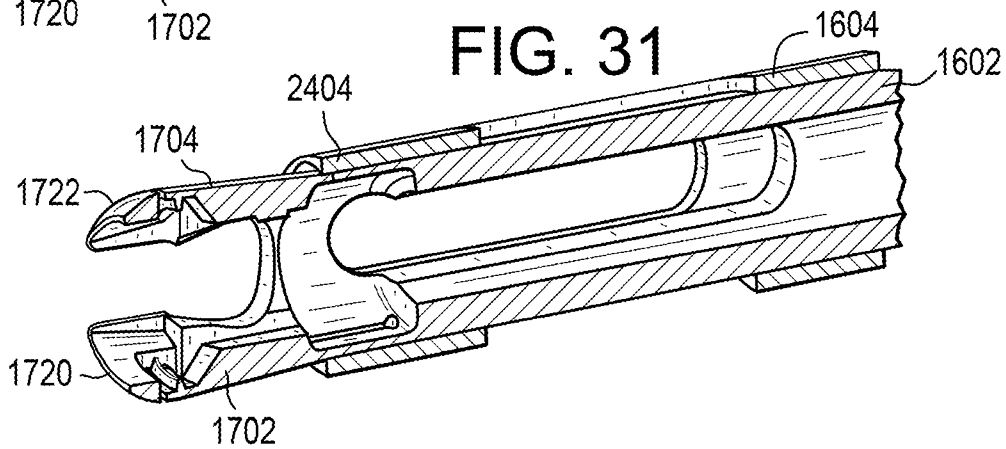
FIG. 31 is a perspective longitudinal cross-sectional view of a distal portion of the instrument of FIG. 16A at a first, proximal-most position relative to the implant engagement member.

FIGS. 30 and 31 show perspective and longitudinal cross-sectional views of the reduction member 1604 disposed over the implant engagement member 1602 at a first, proximal-most position of the reduction member relative to the implant engagement member. In this position, an outer diameter of the implant engagement member 1602 is similar to the inner diameter of the reduction member 1604, so the movable portions 1702, 1704 of each opposed arm 1720, 1722 remain in their resting position. In such a configuration, a rod-receiving head 116 can be passed freely into and out of the space between the opposed arms 1720, 1722.

Figure 32:
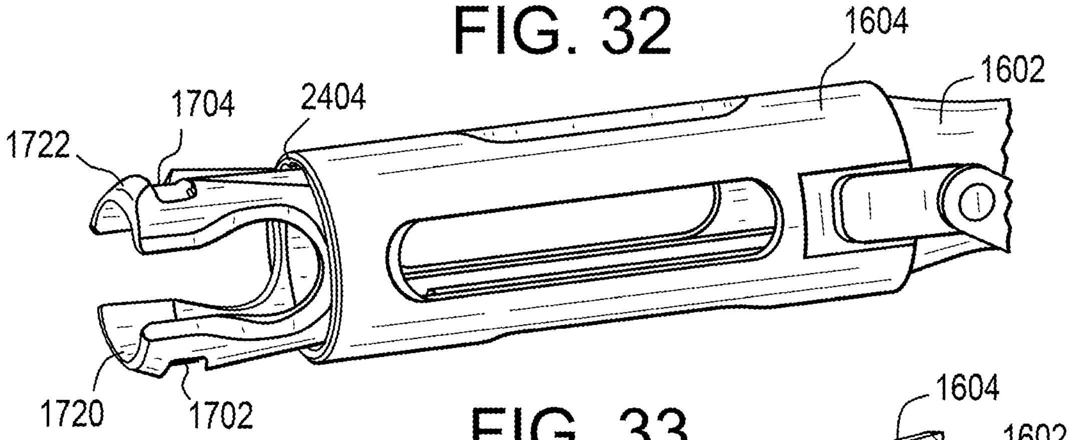
FIG. 32 is a perspective view of a distal portion of the instrument of FIG. 16A at a second, more distal position relative to the implant engagement member.
Figure 33:
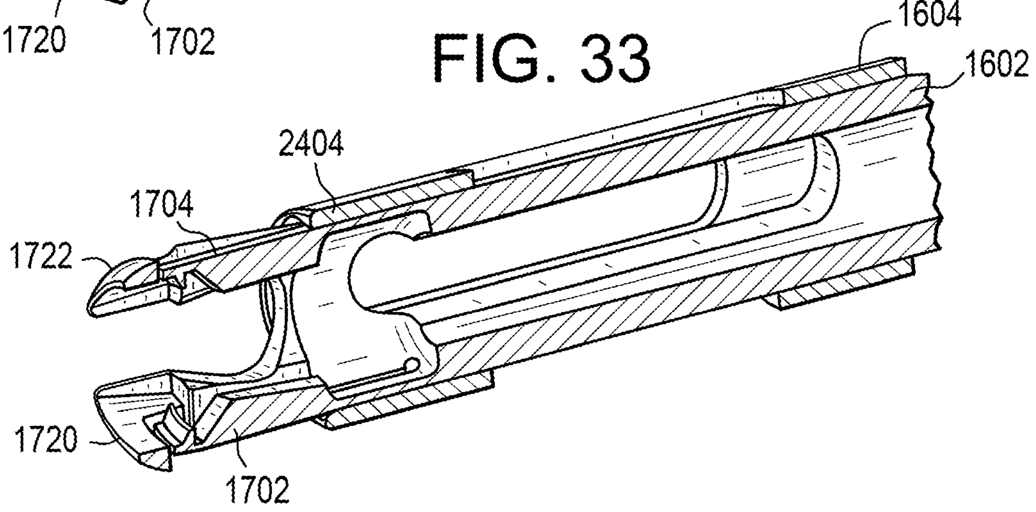
FIG. 33 is a perspective longitudinal cross-sectional view of a distal portion of the instrument of FIG. 16A at a second, more distal position relative to the implant engagement member.

FIGS. 32 and 33 show perspective and longitudinal cross-sectional views of the reduction member 1604 disposed over the implant engagement member 1602 at a second, more distal position of the reduction member relative to the implant engagement member (e.g., as would be achieved when a user begins squeezing the handles 142, 144 toward one another to actuate the device). As the reduction member 1604 begins translating distally over the implant engagement member 1602, it travels over an area having an increased outer diameter. The increased outer diameter of the opposed arms 1720, 1722 can be received within the channels 2402 formed in the inner surface of the reduction member 1604 to allow continued distal movement, but the ridges 2404 formed between the channels 2402 contact the movable portions 1702, 1704 and begin deflecting them radially inward toward a longitudinal axis of the instrument. If a rod-receiving head 116 is disposed between the opposed arms 1720, 1722, the radially inward movement of the movable portions 1702, 1704 can cause the projections 1906 to extend into a groove or other recess formed in the rod-receiving head 116 and securely prevent separation of the head 116 from the implant engagement member 1602.

Figure 34:
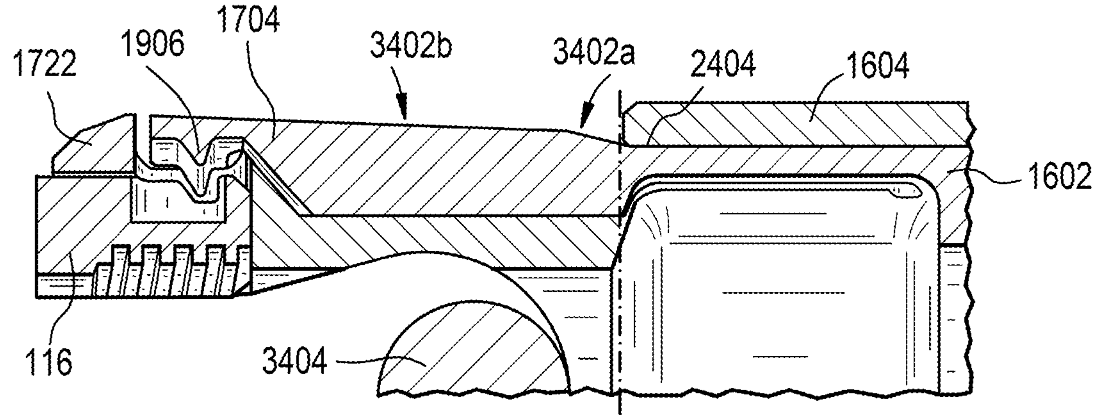
FIG. 34 is a detail side longitudinal cross-sectional view of a distal portion of the instrument of FIG. 16A at a first, proximal-most position relative to the implant engagement member.

Further, the implant engagement member 1602 and its movable portions 1702, 1704 can have particular geometry to facilitate desired movement of the portions 1702, 1704 as the reduction member 1604 is advanced distally. The detail longitudinal cross-sectional view of FIG. 34 illustrates that the movable portion 1704 includes a first outer portion 3402*a* that increases outer diameter in a distal direction at a first, steeper angle and a second outer portion 3402*b* that increases outer diameter in a distal direction at a second, flatter angle (while not shown in the detail view of the figure, the following description can be similar for the movable portion 1702 that is opposite the illustrated movable portion 1704). When the reduction member 1604 is withdrawn proximally, as shown in FIGS. 30, 31, and 34, the ridge 2404 does not deflect the movable portion 1704 radially inward and a rod 3404 and/or rod-receiving head 116 can be passed into the space between the arms 1720, 1722 of the rod engagement member 1602.

Figure 35:
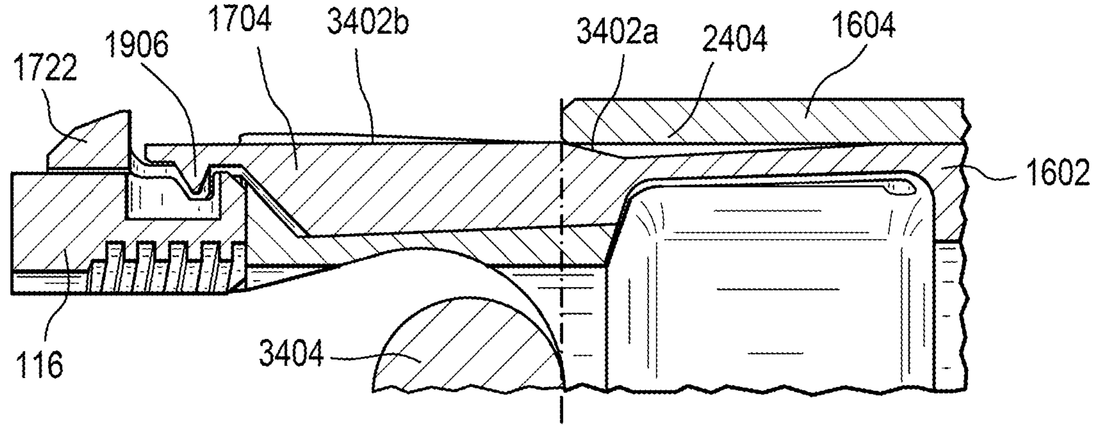
FIG. 35 is a detail side longitudinal cross-sectional view of a distal portion of the instrument of FIG. 16A where the reduction member is distally advanced relative to the position of FIG. 34.

As shown in the detail view of FIG. 35, advancing the reduction member 1604 distally relative to the implant engagement member 1602 causes the ridge 2404 to initially contact the first outer portion 3402*a*. This contact can produce a rapid inward deflection of the movable portion 1704 such that the protrusion 1906 engages with the rod-receiving head 116 or other implant. For example, by the time the reduction member 1604 contacts the rod 3404, the movable portion 1704 can be completely engaged with the implant 116.

Figure 36:
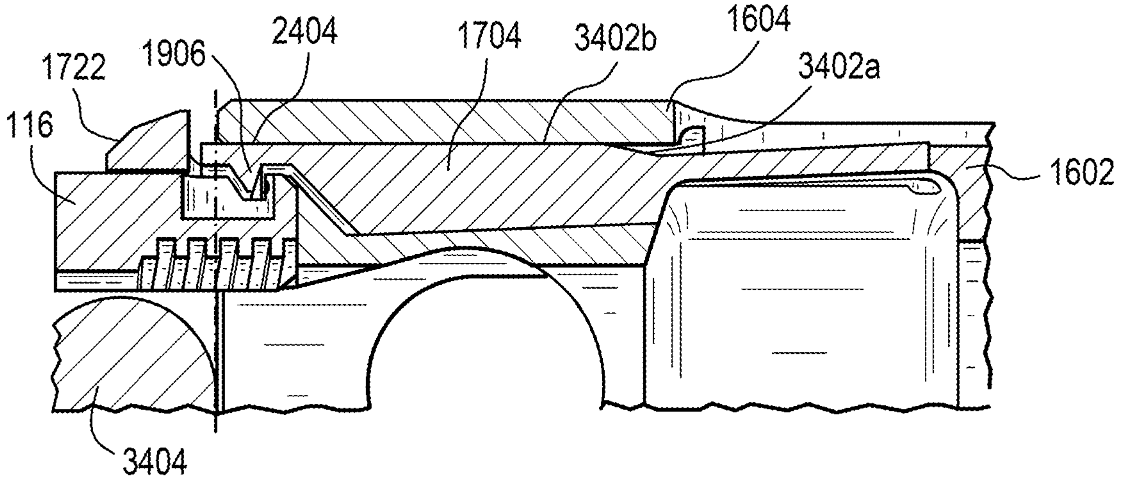
FIG. 36 is a detail side longitudinal cross-sectional view of a distal portion of the instrument of FIG. 16A where the reduction member is further distally advanced relative to the position of FIG. 35.

As shown in FIGS. 35 and 36, as the reduction member 1604 continues to advance relative to the implant engagement member 1602 and reduce the rod 3404, the ridge 2404 rides over the second outer portion 3402*b* having a flatter angle than the first outer portion 3402*a*. The shape of the second outer portion 3402*b* can prevent further inward deflection of the movable portion 1704 during rod reduction.

Figure 37:
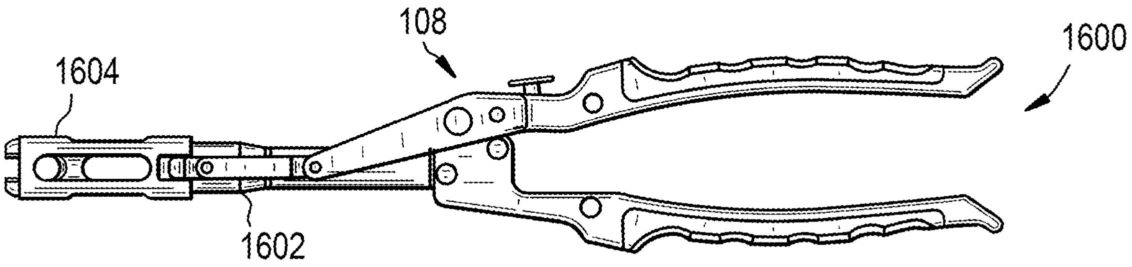
FIG. 37 is a side perspective view of the instrument of FIG. 16A in a locked configuration.
Figure 38:
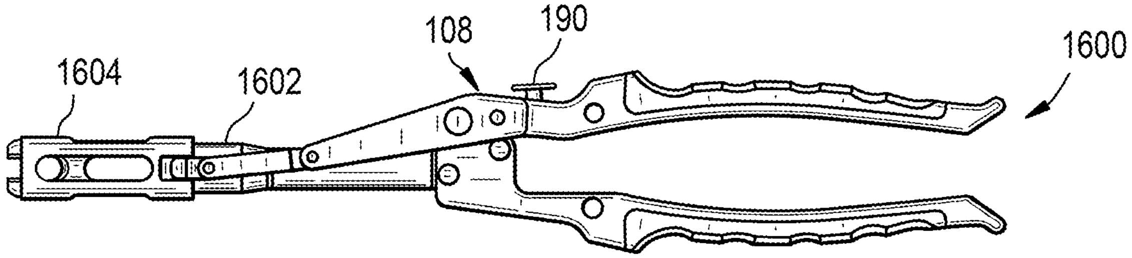
FIG. 38 is a side perspective view of the instrument of FIG. 16A in a final state of distal advancement of the reduction member relative to the implant engagement member.
Figure 39:
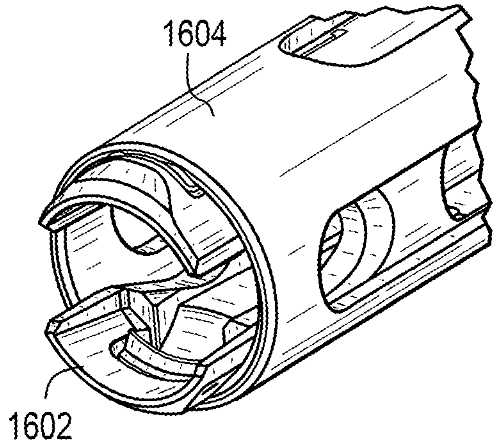
FIG. 39 is a detail perspective view of a distal portion of the instrument of FIG. 16A in a locked configuration.

FIGS. 37-40 illustrate further states of distal advancement of the reduction member 1604 relative to the implant engagement member 1602. FIGS. 37 and 39, for example, illustrate the instrument 1600 in a locked configuration similar to that shown in FIGS. 9A-9C, as well as the detail view of FIG. 36. In this configuration, the reduction member 1604 has been advanced distally along the implant engagement member 1602 to reduce a spinal rod in contact with a distal end thereof and the locking mechanism 108 has been engaged to maintain a position of the instrument.

Figure 40:
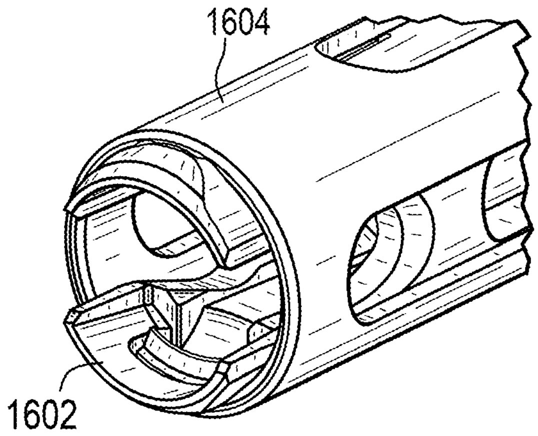
FIG. 40 is a detail perspective view of a distal portion of the instrument of FIG. 16A in a final state of distal advancement of the reduction member relative to the implant engagement member.

FIGS. 38 and 40 illustrate a final state of distal advancement of the reduction member 1604 relative to the implant engagement member 1602. In these figures, the reduction member 1604 is advanced distally to a maximum extent relative to the implant engagement member 1602. This configuration is similar to that shown in FIG. 12 and described above, and can be utilized to release tension that may be on the lock mechanism pawl and allow an easier release of the pawl from its groove when the release button 190 is depressed. Alternatively or in addition, a user can utilize this feature to aid in set screw insertion and tightening to help reduce the rod a final degree with regard to the bone anchor.

Figure 16:
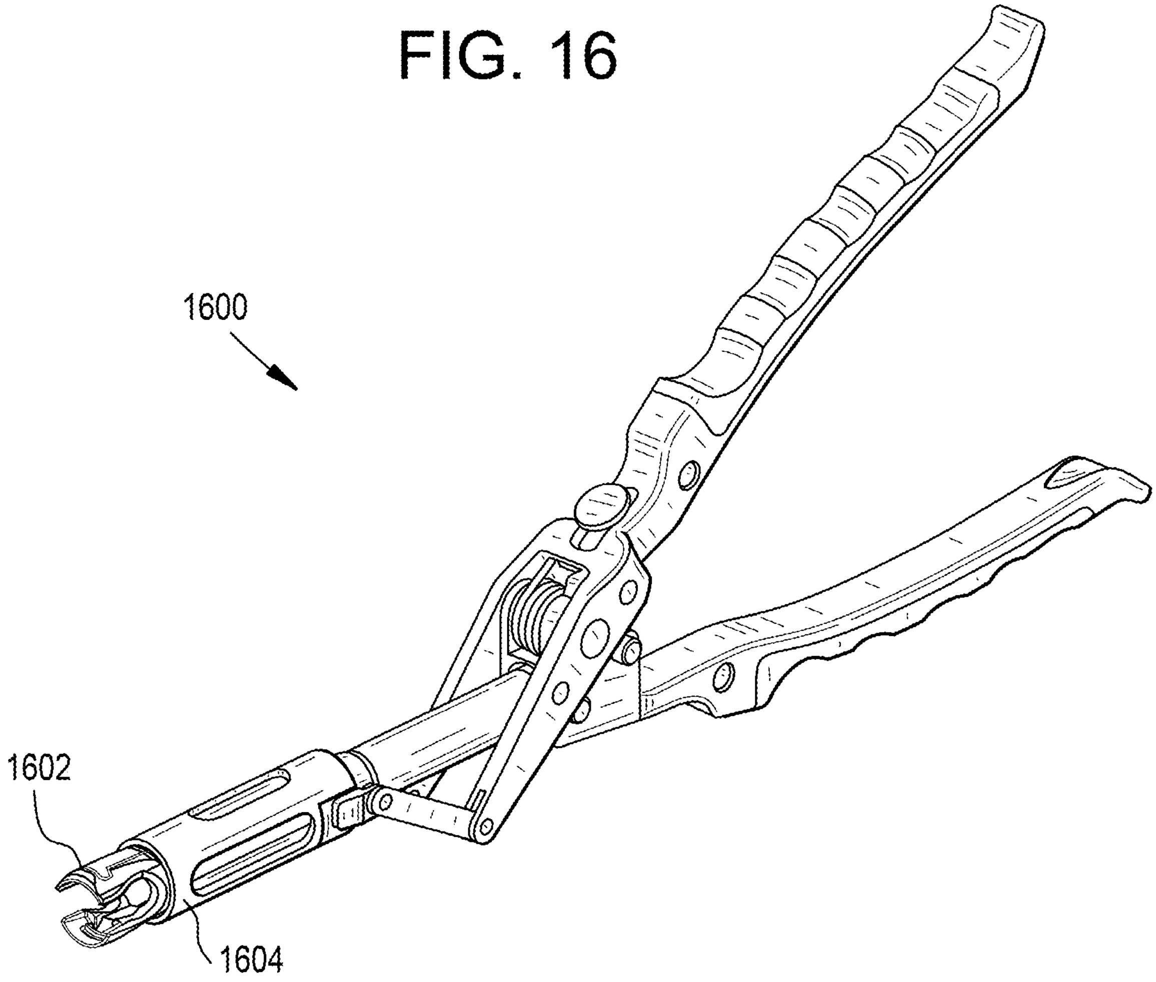
FIG. 16 is a perspective view of one embodiment of a reducer instrument according to the present disclosure.
Figure 41:
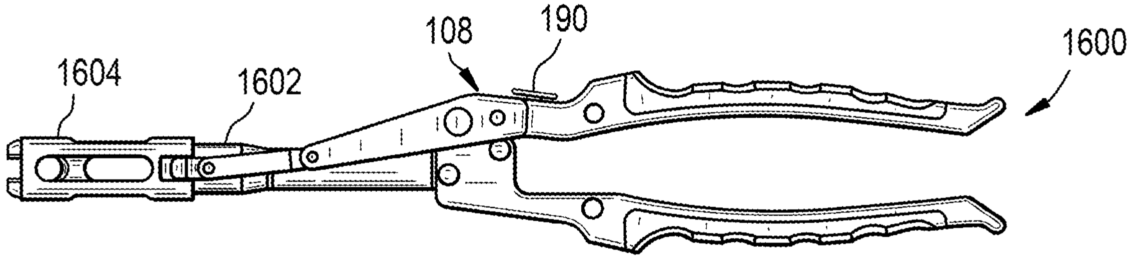
FIG. 41 is a side perspective view of the instrument of FIG. 16A being released from a locked configuration.

FIG. 41 illustrates actuation of the release button 190 that can release the lock mechanism and allow the instrument 1600 to move from the configuration shown in FIG. 41 to the open configuration shown in FIG. 16 wherein the reduction member 1604 is withdrawn proximally relative to the implant engagement member 1602. Upon withdrawal of the reduction member 1604 proximally, the movable portions 1702, 1704 will return to their resting positions as shown in FIG. 23, which will clear the inwardly-extending protrusions 1906 from any groove or other recess formed in a rod-receiving head 116 disposed between the opposed arms 1720, 1722, thereby allowing the head to be separated from the instrument 1600 and another head loaded for coupling.

Various devices disclosed herein can be constructed from any of a variety of known materials. Example materials include those which are suitable for use in surgical applications, including metals such as stainless steel, titanium, nickel, cobalt-chromium, or alloys and combinations thereof, polymers such as PEEK, ceramics, carbon fiber, and so forth. Further, various methods of manufacturing can be utilized, including 3D printing or other additive manufacturing techniques, as well as more conventional manufacturing techniques, including molding, stamping, casting, machining, etc.

Various devices and methods disclosed herein can be used in minimally-invasive surgery and/or open surgery. While various devices and methods disclosed herein are generally described in the context of surgery on a human patient, the methods and devices disclosed herein can be used in any of a variety of surgical procedures with any human or animal subject, or in non-surgical procedures.

Various devices or components disclosed herein can be designed to be disposed of after a single use, or they can be designed to be used multiple times. In either case, however, various devices or components can be reconditioned for reuse after at least one use. Reconditioning can include any combination of the steps of disassembly, followed by cleaning or replacement of particular pieces, and subsequent reassembly. In particular, a device or component can be disassembled, and any number of the particular pieces or parts thereof can be selectively replaced or removed in any combination. Upon cleaning and/or replacement of particular parts, the device or component can be reassembled for subsequent use either at a reconditioning facility, or by a surgical team immediately prior to a surgical procedure. Reconditioning of a device or component can utilize a variety of techniques for disassembly, cleaning/replacement, and reassembly. Use of such techniques, and the resulting reconditioned device, are all within the scope of the present disclosure.

Various devices or components described herein can be processed before use in a surgical procedure. First, a new or used device or component can be obtained and, if necessary, cleaned. The device or component can then be sterilized. In one sterilization technique, the device or component can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the device or component and in the container. The sterilized device or component can then be stored in the sterile container. The sealed container can keep the device or component sterile until it is opened in the medical facility. Other forms of sterilization are also possible, including beta or other forms of radiation, ethylene oxide, steam, or a liquid bath (e.g., cold soak). Certain forms of sterilization may be better suited to use with different devices or components, or portions thereof, due to the materials utilized, the presence of electrical components, etc.

In this disclosure, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B," "one or more of A and B," and "A and/or B" are each intended to mean "A alone, B alone, or A and B together." A similar interpretation is also intended for lists including three or more items. For example, the phrases "at least one of A, B, and C," "one or more of A, B, and C," and "A, B, and/or C" are each intended to mean "A alone, B alone, C alone, A and B together, A and C together, B and C together, or A and B and C together." In addition, use of the term "based on," is intended to mean, "based at least in part on," such that an un-recited feature or element is also permissible.

Further features and advantages based on the above-described embodiments are possible and within the scope of the present disclosure. Accordingly, the disclosure is not to be limited by what has been particularly shown and described. All publications and references cited herein are expressly incorporated herein by reference in their entirety, except for any definitions, subject matter disclaimers or disavowals, and except to the extent that the incorporated material is inconsistent with the express disclosure herein, in which case the language in this disclosure controls.

Examples of the above-described embodiments can include the following:

1. A surgical instrument, comprising:
   - a first handle having a proximal grip portion and a distal housing with a lumen extending therethrough;
   - opposed arms extending distally from the housing that are configured to interface with an implant;

a reducer sleeve disposed around the opposed arms and configured to translate relative thereto;

a second handle having a proximal grip portion, the second handle being pivotably coupled to the housing and the reducer sleeve such that moving the second handle toward the first handle causes distal translation of the reducer sleeve relative to the opposed arms;

a pawl pivotably coupled to the second handle distal to the grip portion, the pawl being configured to ride over a portion of the housing that includes a groove as the second handle is moved toward the first handle;

wherein the pawl is configured to seat in the groove and maintain a relative position of the first and second handles when the second handle is moved sufficiently toward the first handle.

2. The instrument of claim 1, further comprising a button extending from the pawl and configured to move the pawl clear of the groove when depressed.

3. The instrument of any of claims 1 to 2, further comprising a spring urging a distal portion of the pawl into the portion of the housing that includes the groove.

4. The instrument of any of claims 1 to 4, wherein the opposed arms define a tapering slot therebetween having a first distance between the opposed arms at a distal portion of the slot that is greater than a second distance between the opposed arms at a proximal portion of the slot.

5. The instrument of any of claims 1 to 4, wherein a distal end of at least one of the opposed arms includes a protrusion configured to extend into a recess of the implant.

6. The instrument of any of claims 1 to 5, wherein distal translation of the reducer sleeve relative to the opposed arms moves the opposed arms toward one another.

7. The instrument of any of claims 1 to 6, further comprising one or more links pivotably coupled to the second handle and the reducer sleeve.

8. The instrument of any of claims 1 to 7, further comprising a biasing element urging the first and second handle away from one another.

9. The instrument of any of claims 1 to 8, wherein the housing includes at least one protrusion formed thereon that abuts against the second handle at a fully open or a fully closed position of the first and second handles relative to one another.

10. The instrument of claim 9, wherein the at least one protrusion includes a first protrusion that abuts against the second handle at a fully closed position of the first and second handles, and wherein the first protrusion is separated from the second handle when the pawl is seated in the groove and maintaining a relative position of the first and second handles.

11. A surgical method, comprising:

positioning opposed arms of a reducer instrument around a portion of an implant;

moving first and second handles of the reducer instrument toward one another until a pawl coupled to the second handle seats within a groove formed in a housing of the first handle to maintain a relative position of the first and second handles;

wherein moving the first and second handles of the reducer instrument toward one another causes a reducer sleeve disposed around the opposed arms to translate distally relative thereto;

wherein distal translation of the reducer sleeve causes the opposed arms of the reducer instrument to move toward one another and couple with the implant, and also causes a spinal fixation element to translate distally into a receiving portion of the implant.

12. The method of claim 11, wherein moving the first and second handles of the reducer instrument toward one another includes overcoming a biasing force urging the handles away from one another.

13. The method of any of claims 11 to 12, further comprising locking the spinal fixation element relative to the implant while the reducer instrument maintains a position of the spinal fixation element relative to the implant.

14. The method of claim 13, wherein locking the spinal fixation element relative to the implant includes inserting a set screw through a bore formed in the reducer instrument and coupling the set screw with the implant.

15. The method of claim 14, further comprising further reducing the spinal fixation element distally into the receiving portion of the implant using the set screw such that compressive forces between the reducer sleeve and spinal fixation element are reduced.

16. The method of any of claims 11 to 15, further comprising moving the first and second handles of the reducer instrument toward one another beyond a position at which the pawl seats within the groove of the housing until one of the first and second handles contacts a stop formed on the other handle.

17. The method of any of claims 11 to 16, further comprising depressing a button to move the pawl clear of the groove and allow movement of the first and second handles away from one another.

18. The method of claim 17, further comprising moving the first and second handles of the reducer instrument away from one another to proximally translate the reducer sleeve relative to the opposed arms and allow the opposed arms to move away from one another and release from the implant.

19. The method of claim 18, further comprising repeating the method across a plurality of implants disposed along a patient's spine.

20. A surgical method, comprising:

positioning an instrument in an unlocked configuration, the instrument having an implant engagement member, a reduction member having a channel therein for receiving the implant engagement member therethrough, a handle assembly being coupled to the reduction member and receiving the implant engagement member through a bore thereof, and a lock having a pawl disposed outside of a groove formed in the handle assembly, the handle assembly including a pair of handles pivotably coupled to one another;

positioning an implant between opposed arms of the implant engagement member; and moving the pair of handles toward one another to position the instrument in a locked configuration;

wherein moving the pair of handles toward one another distally advances the reduction member relative to the implant engagement member to reduce a spinal fixation element into a receiving portion of the implant and moves the pawl into the groove of the handle assembly.

21. The method of claim 20, wherein moving the pair of handles toward one another includes overcoming a biasing force on the pair of handles and causing a linkage disposed between the pair of handles and the reduction member to advance the reduction member distally.

22. The method of any of claims 20 to 21, further comprising actuating a button coupled to the pawl to disengage the pawl from the groove and allow return of the device from the locked configuration to the unlocked configuration.

23. The method of any of claims 20 to 22, further comprising delivering a set screw to the implant through the bore of the handle assembly.

24. The instrument of any of claims 1 to 10, wherein each opposed arm includes a movable portion configured to deflect radially inward relative to the arm.

25. The instrument of claim 24, wherein the reducer sleeve includes a feature formed on an inner surface thereof that is configured to contact the movable portion of each opposed arm.

26. The instrument of any of claims 24 to 25, wherein each movable portion includes an inwardly-extending projection.

27. The method of any of claims 20 to 23, wherein distally advancing the reduction member relative to the implant engagement member deflects movable portions of each of the opposed arms of the implant engagement member radially inward such that the movable portions extend into a recess formed in the implant.

28. A surgical method, comprising:
positioning opposed arms of a reducer instrument around a portion of an implant;
moving first and second handles of the reducer instrument toward one another until a pawl coupled to the second handle seats within a groove formed in a housing of the first handle to maintain a relative position of the first and second handles;
wherein moving the first and second handles of the reducer instrument toward one another causes a reducer sleeve disposed around the opposed arms to translate distally relative thereto;
wherein distal translation of the reducer sleeve causes movable portions of the opposed arms of the reducer instrument to move toward one another and couple with the implant, and also causes a spinal fixation element to translate distally into a receiving portion of the implant.

What is claimed is:

1. A surgical instrument, comprising:
a first handle having a proximal grip portion and a distal housing with a lumen extending from a proximal end to a distal end of the housing to define a length of the housing;
opposed arms extending distally from the housing that are configured to interface with an implant;
a reducer sleeve disposed around the opposed arms and configured to translate relative thereto;
a second handle having a proximal grip portion, the second handle being pivotably coupled to the housing along its length and the reducer sleeve such that moving the second handle toward the first handle causes distal translation of the reducer sleeve relative to the opposed arms;
a pawl pivotably coupled to the second handle distal the proximal grip portion of the second handle, the pawl being configured to ride over a portion of the length of the housing that includes a groove as the second handle is moved toward the first handle;
wherein the pawl is configured to seat in the groove and maintain a relative position of the first and second handles when the second handle is moved sufficiently toward the first handle.

2. The instrument of claim 1, further comprising a button extending from the pawl and configured to move the pawl clear of the groove when depressed.

3. The instrument of claim 1, further comprising a spring urging a distal portion of the pawl into the portion of the housing that includes the groove.

4. The instrument of claim 1, wherein the opposed arms define a tapering slot therebetween having a first distance between the opposed arms at a distal portion of the slot that is greater than a second distance between the opposed arms at a proximal portion of the slot.

5. The instrument of claim 1, wherein a distal end of at least one of the opposed arms includes a protrusion configured to extend into a recess of the implant.

6. The instrument of claim 1, wherein distal translation of the reducer sleeve relative to the opposed arms moves the opposed arms toward one another.

7. The instrument of claim 1, further comprising one or more links pivotably coupled to the second handle and the reducer sleeve.

8. The instrument of claim 1, further comprising a spring or torsion spring urging the first and second handle away from one another.

9. The instrument of claim 1, wherein the housing includes at least one protrusion formed thereon that abuts against the second handle at a fully open or a fully closed position of the first and second handles relative to one another.

10. The instrument of claim 9, wherein the at least one protrusion includes a first protrusion that abuts against the second handle at a fully closed position of the first and second handles, and wherein the first protrusion is separated from the second handle when the pawl is seated in the groove and maintaining a relative position of the first and second handles.

11. A surgical method, comprising:
positioning an instrument in an unlocked configuration, the instrument having an implant engagement member, a reduction member having a channel therein for receiving the implant engagement member therethrough, a handle assembly being coupled to the reduction member and receiving the implant engagement member through a bore formed in a distal portion of the handle assembly, and a lock having a pawl disposed outside of a groove formed in the distal portion of the handle assembly, the handle assembly including a pair of handles pivotably coupled to one another;
positioning an implant between opposed arms of the implant engagement member; and
moving the pair of handles toward one another to position the instrument in a locked configuration;
wherein moving the pair of handles toward one another distally advances the reduction member relative to the implant engagement member to reduce a spinal fixation element into a receiving portion of the implant and moves the pawl into the groove of the handle assembly.

12. The method of claim 11, wherein moving the pair of handles toward one another includes overcoming a biasing force on the pair of handles and causing a linkage disposed between the pair of handles and the reduction member to advance the reduction member distally.

13. The method of claim 11, further comprising actuating a button coupled to the pawl to disengage the pawl from the groove and allow return of the device from the locked configuration to the unlocked configuration.

14. The method of claim 11, further comprising delivering a set screw to the implant through the bore of the handle assembly.

15. The instrument of claim 1, wherein each opposed arm includes a movable portion configured to deflect radially inward relative to the arm.

16. The instrument of claim 15, wherein the reducer sleeve includes a central ridge formed on an inner surface thereof that is configured to contact the movable portion of each opposed arm.

17. The instrument of claim 15, wherein each movable portion includes an inwardly-extending projection.

18. The method of claim 11, wherein distally advancing the reduction member relative to the implant engagement member deflects movable portions of each of the opposed arms of the implant engagement member radially inward such that the movable portions extend into a recess formed in the implant.

* * * * *